(12) United States Patent
Ptashne et al.

(10) Patent No.: US 7,087,711 B2
(45) Date of Patent: Aug. 8, 2006

(54) TRANSCRIPTIONAL ACTIVATOR COMPRISING A SHORT HYDROPHOBIC ACTIVATION PEPTIDE

(75) Inventors: Mark Ptashne, Cambridge, MA (US); Xiangyang Lu, Cambridge, MA (US); Yibing Wu, Wellesley, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 722 days.

(21) Appl. No.: 09/943,944

(22) Filed: Aug. 31, 2001

(65) Prior Publication Data

US 2004/0014036 A1    Jan. 22, 2004

(51) Int. Cl.
*C07K 19/00*    (2006.01)
*C07K 14/00*    (2006.01)

(52) U.S. Cl. .................. 530/300; 530/324; 530/350
(58) Field of Classification Search ................ 530/300, 530/324, 350
See application file for complete search history.

(56) References Cited

U.S. PATENT DOCUMENTS 6,326,166 B1 *  12/2001  Pomerantz et al. ........ 435/69.1

\* cited by examiner

*Primary Examiner*—Terry McKelvey
(74) *Attorney, Agent, or Firm*—Choate Hall & Stewart LLP

(57) ABSTRACT

The present invention describes novel transcriptional activators and activation systems. The activators of the present invention comprise a DNA binding moiety linked to a short peptide of novel sequence. Preferably, the peptide is substantially hydrophobic. Preferred peptides include at least one aromatic amino acid. The present invention also provides improved transcriptional activation systems, useful for the identification and characterization of protein—protein interactions. The invention also describes the production and use of certain TBP mutants that enhance transcriptional activation by some activators.

3 Claims, 8 Drawing Sheets

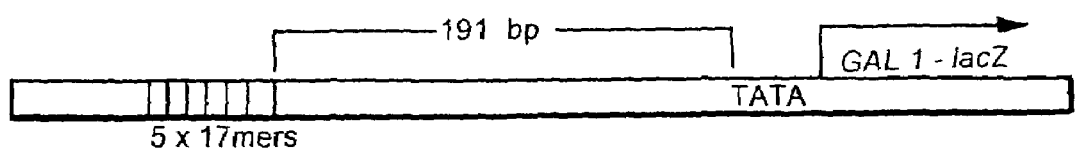
| Construct | β-gal activity |
|---|---|
| GAL 4 (1-881) | 2300 |
| GAL 4 (1-100) | 2 |
| GAL 4 (1-100) + Y L L P T C I P | 4400 |
| + L I C Y P L P T | 100 |
| + I P L Y L T C P | 17 |
F I G. 1

| Construct | | | β-gal. activity |
|---|---|---|---|
| GAL 4 (1-881) | | | 2800 |
| GAL 4 (1- | 91<br>A L L T G L F V Q D 100) | | 2 |
| GAL 4 (1- | 100<br>A L L T G L F V Q D | ⎯ 8mer ⎯<br>+ Y L L P T C I P | 4400 |
| | A L L T G L F V Q ☐ | + Y L L P T C I P | 120 |
| | A L L T G L F V ☐ D | + Y L L P T C I P | 450 |
| | A L L T G L F ☐ Q D | + Y L L P T C I P | 3 |
| | A L L T G L ☐ V Q D | + Y L L P T C I P | 2 |
| | A L L T G ☐ F V Q D | + Y L L P T C I P | 3 |
| | A L L T G L F V Q [A] | + Y L L P T C I P | 4200 |
| | A L L T G L F V [A] D | + Y L L P T C I P | 3800 |
| | A L L T G L F [A] Q D | + Y L L P T C I P | 100 |
| | A L L T G L [A] V Q D | + Y L L P T C I P | 30 |

TRANSCRIPTIONAL ACTIVATOR COMPRISING A SHORT HYDROPHOBIC ACTIVATION PEPTIDE

GOVERNMENT SUPPORT

The work described herein was supported by United States government grant number GM32308-14 from the National Institutes of Health. The United States government may have certain rights in the invention.

RELATED APPLICATION

The present application is a Continuation-in-part of co-pending application No. 60/017,016, filed May 3, 1996, the entire contents of which are incorporated herein by reference.

BACKGROUND OF THE INVENTION

Gene activation requires interaction of DNA-bound activators with proteins binding near the transcription start site of a gene (Ptashne, Nature 335:983, 1988). In eukaryotes, activation of RNA polymerase II genes requires many transcription factors in addition to RNA polymerase. Transcriptional activators have been shown to contact one or another of these transcription factors, including TATA-binding protein (TBP), TBP-associated factors (TAFs), TFIIB, and TFIIH (Roeder, Trends Biochem. Sci. 16:402, 1991; Zawel et al., Prog. Nucl. Acids Res. Mol. Biol. 44:67, 1993; Conaway et al., Annu. Rev. Biochem. 62:161, 1993; Hoey et al., Cell 72:247). Thus, it has been proposed that transcription initiation involves a multistep assembly process, various steps of which might be catalyzed by activators (Buratowski et al., Cell 56:549, 1989; Choy et al., Nature 366:531, 1993).

Some transcriptional activators are thought to recruit one or more transcription factors to the DNA, to cause crucial conformational changes in target proteins and thereby to facilitate the complex process of assembling the transcriptional machinery, or both (Lin et al., Cell 64:971, 1991; Roberts et al., Nature 371:717, 1994; Hori et al., Curr. Op. Genet. Dev. 4:236, 1994). Also, given the observation that yeast RNA polymerase II is associated with several transcription factors, in a complex termed the "holoenzyme", it has been proposed that some transcriptional activators might function by recruiting the holoenzyme complex to DNA (Koleske et al., Nature 368:466, 1994; Kim et al., Cell 77:599, 1994; Carey, Nature 368:402, 1994).

Transcriptional activation has been much studied both in the context of controlling gene expression in cells, for example so that principles of gene activation can be employed in genetic therapies, and as an experimental tool for analysis of protein—protein interactions in cells (Fields et al., Nature 340:245, 1989; Gyuris et al., Cell 75:791, 1993). One difficulty that has been encountered in the use and analysis of transcriptional activation systems, however, is that over-expression of transcriptional activators in cells typically inhibits gene expression, sometimes with dire results on the cells. This effect, termed "squelching", apparently represents the titration of a transcription factor by the over-expressed transcriptional activator (Gill et al., Nature 334:721, 1988). Another difficulty that has been encountered specifically in the protein—protein interaction applications is that useful controls are often unavailable, so that spurious results are often observed. Also, the protein—protein interaction systems are typically not useful for identification of proteins that interact with transcriptional activators themselves. Given that transcriptional activators represent a significant fraction of all known proteins, this limitation of existing systems presents a serious problem.

There remains a need for the identification of novel transcriptional activators and improved transcriptional activation systems. In particular, there is a need for strong transcriptional activators that do not "squelch" other known activators, and for protein—protein interaction systems useful for identifying interaction partners of transcriptional activators.

SUMMARY OF THE INVENTION

The present invention provides novel transcriptional activators. In particular, the invention provides activators in which a short peptide having activating capability is linked to a DNA binding domain. The peptides do not correspond to fragments of known transcriptional activators (that is, their sequences are not found in the SwissProt database). Moreover, the peptides apparently activate transcription by a novel mechanism as they do not squelch known activators when they are over expressed in yeast. Without wishing to be bound by any particular theory, we propose that these activators function by interacting with a component of the RNA polymerase II holoenzyme; this hypothesis is consistent with the observation that the only other transcriptional activator known not to squelch is Gal11, which is part of the holoenzyme (see Barberis et al., Cell, 81:359, 1995). The present invention also provides methods of identifying, characterizing, and using such novel transcriptional activators. In particular, the invention provides methods of activating transcription by providing such a novel activator to a cell.

The present invention also provides novel transcriptional activation systems, each based on the idea of exploiting non-conventional transcriptional activators. The systems described herein utilize holoenzyme components, or factors that interact therewith, in a way that provides advantages over known transcriptional activation systems. For example, we provide protein—protein interaction systems that utilize Gal11 and/or Gal11P to overcome some of the above-mentioned difficulties with standard di-hybrid and interaction trap systems.

The present invention also provides novel TBP mutants that increase transcriptional activation by certain activators. The particular TBP mutants described enhance activation by Gal11 more than they enhance activation by Gal4 region II. The invention also provides methods of identifying, characterizing, and using such TBP mutants.

DESCRIPTION OF THE DRAWINGS

FIG. 1 demonstrates the dependence between transcriptional activation and the order of amino acids in the inventive peptide activator, SEQ ID NO: 167. Peptides having the same composition as SEQ ID NO: 167, but different sequence orders, such as SEQ ID NO: 226 and SEQ ID NO: 227, produce substantially lower b-gal activity levels. As indicated, SEQ ID NO: 167 produces a β-gal activity level of 4400, while SEQ ID NO: 226 and SEQ ID NO: 227 produce β-gal activities of 100 and 17 respectively.

mutagenized domains are listed consecutively from SEQ ID NO: 229 through SEQ ID NO: 237.

Figure 3:
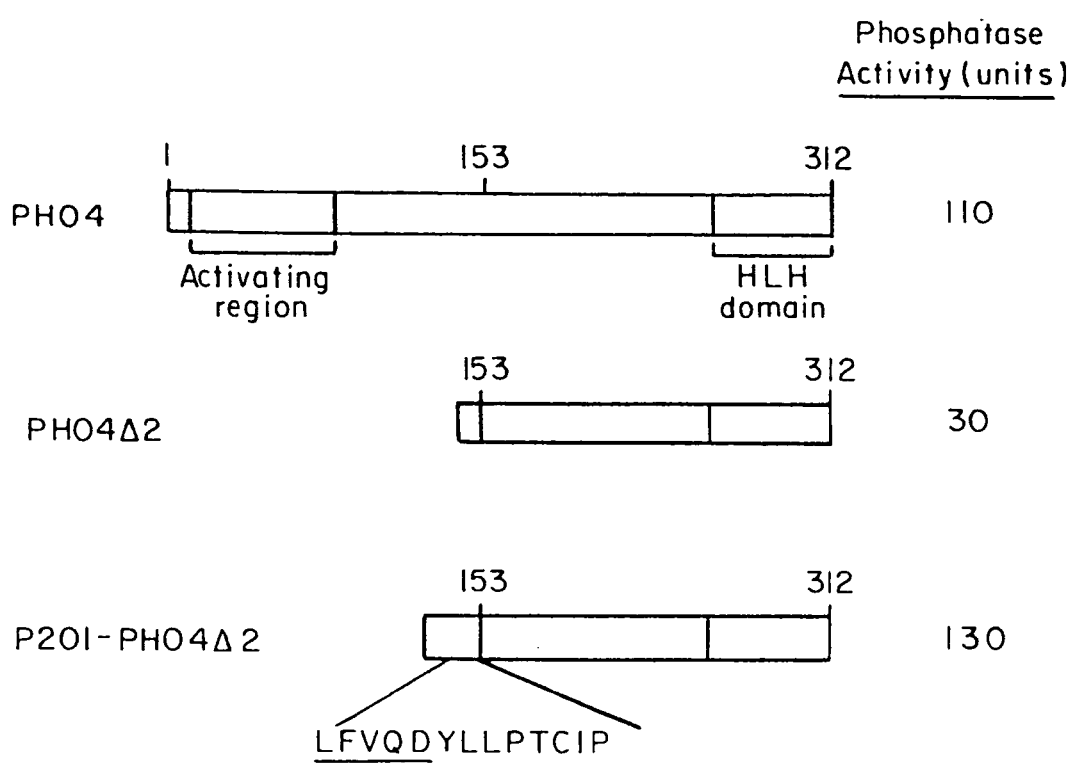

FIG. 3 shows transcriptional activation by SEQ ID NO: 238, comprising Gal4 residues 96–100 and SEQ ID NO: 167, when linked to the Pho4 binding domain.

Figure 4:
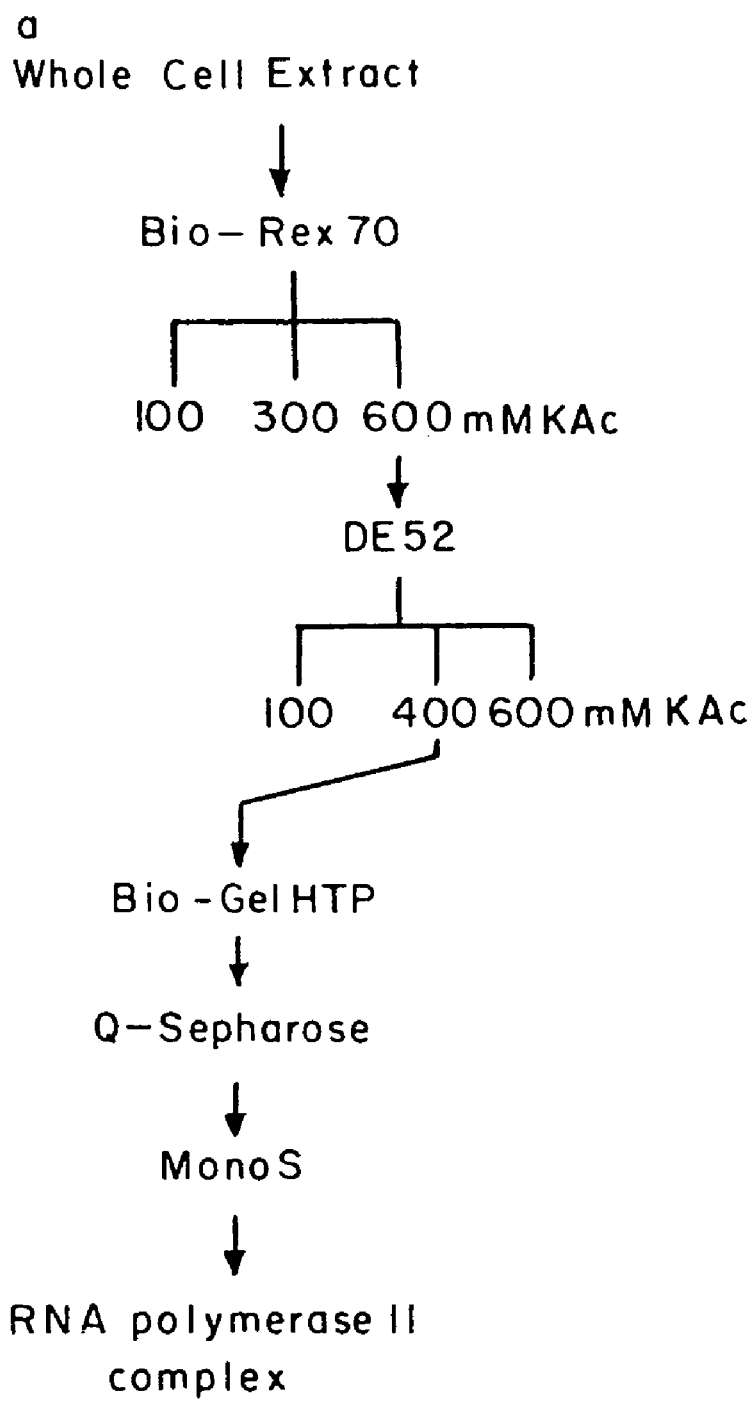

FIG. 4 depicts the purification scheme used for yeast holoenzyme preparations.

Figure 5:
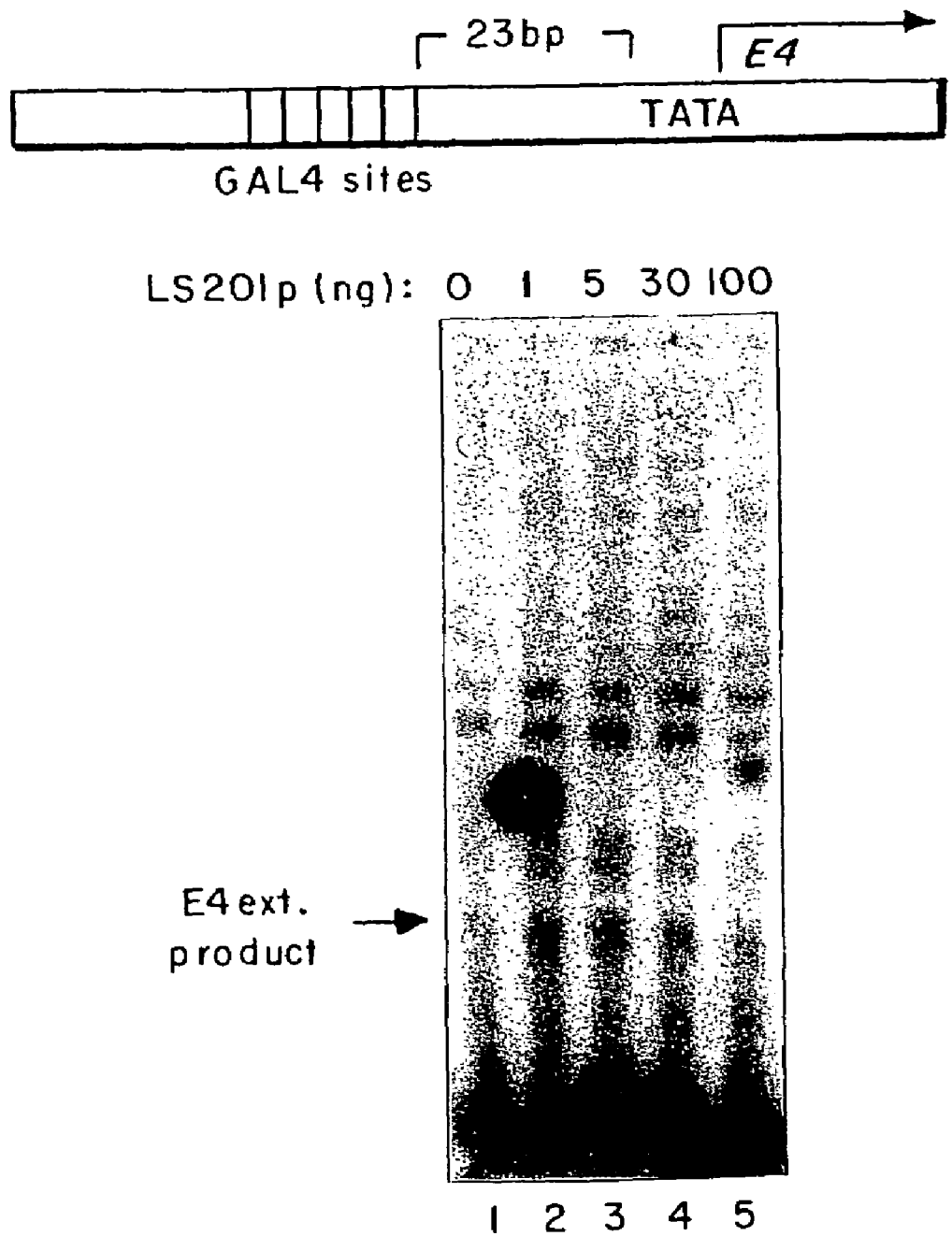

FIG. 5 shows in vitro transcriptional activation by Gal4-LS201 in a yeast nuclear extract.

Figure 6:
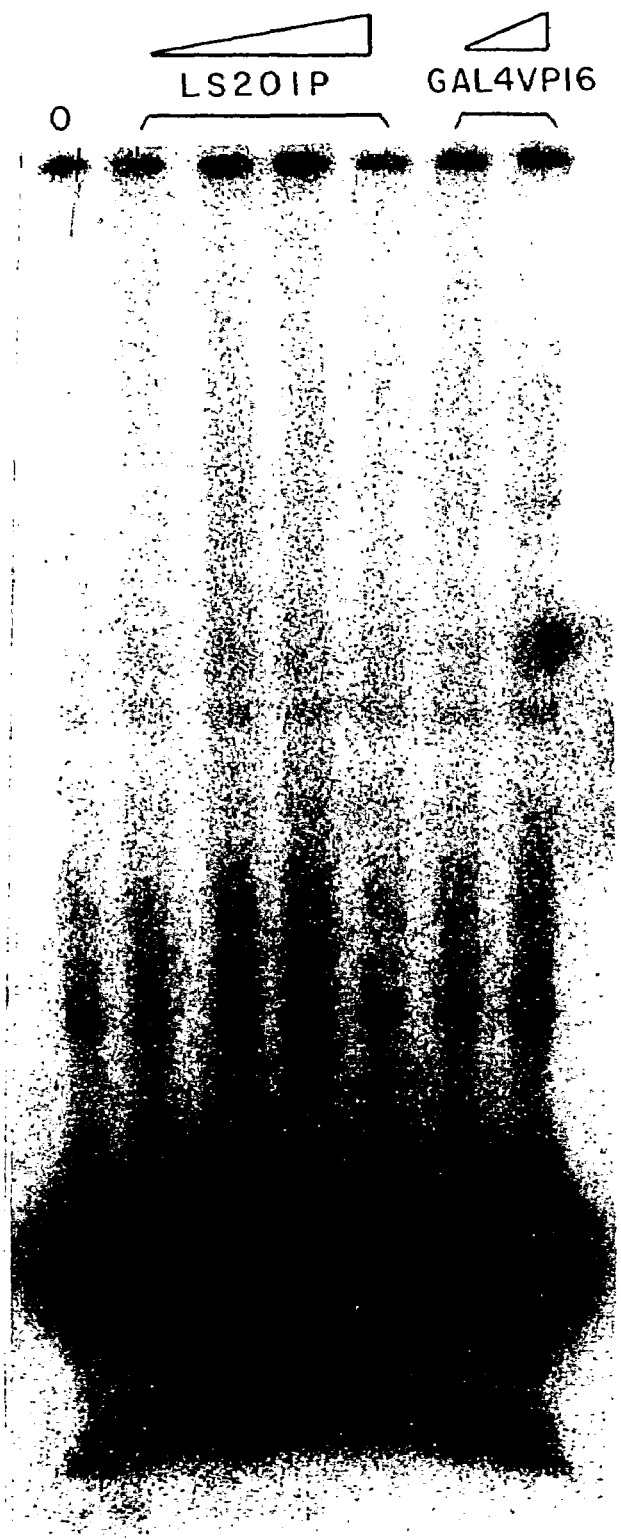

FIG. 6 shows in vitro transcriptional activation by Gal4-LS201 on the yeast holoenzyme.

Figure 7:
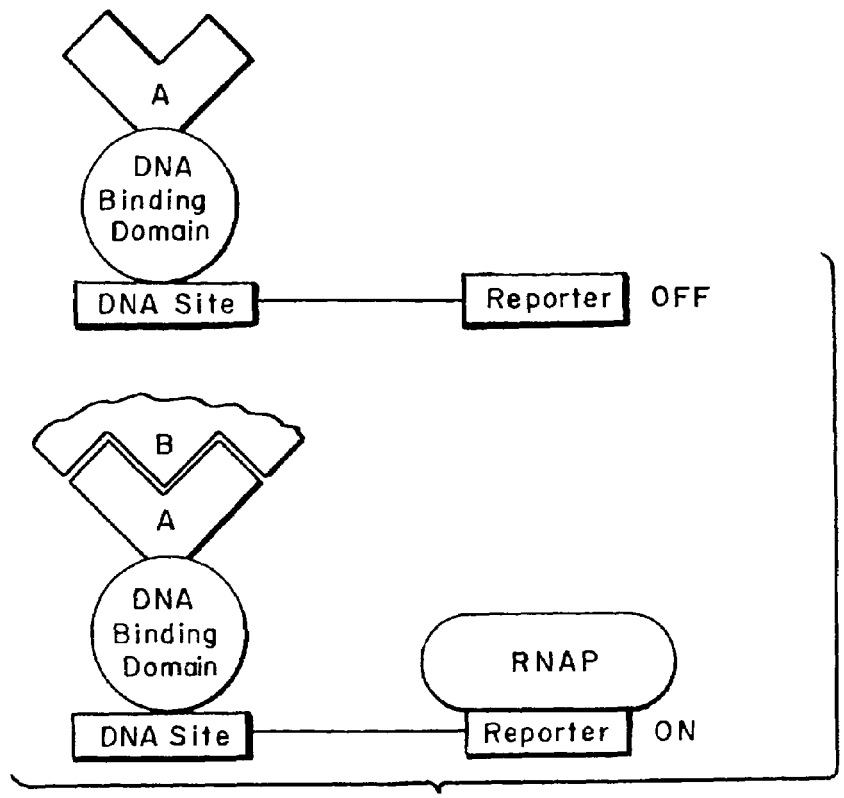

FIG. 7 is a schematic of a standard protein—protein interaction transcriptional activation assay.

Figure 8:
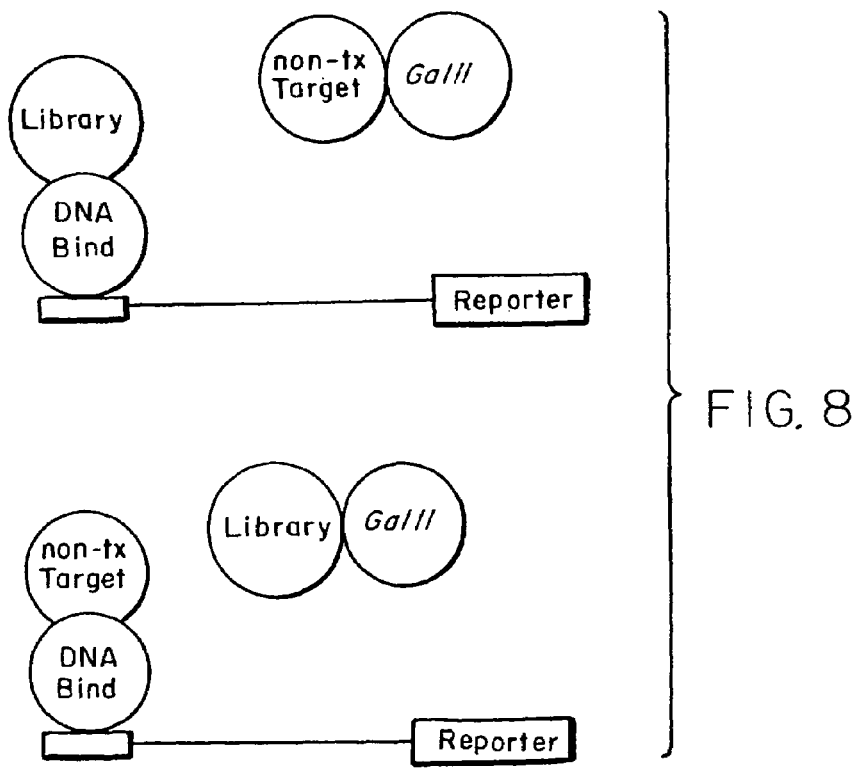

FIG. 8 is a schematic of a protein—protein interaction transcriptional activation assay employing Gal11 as the activation domain.

Figure 9:
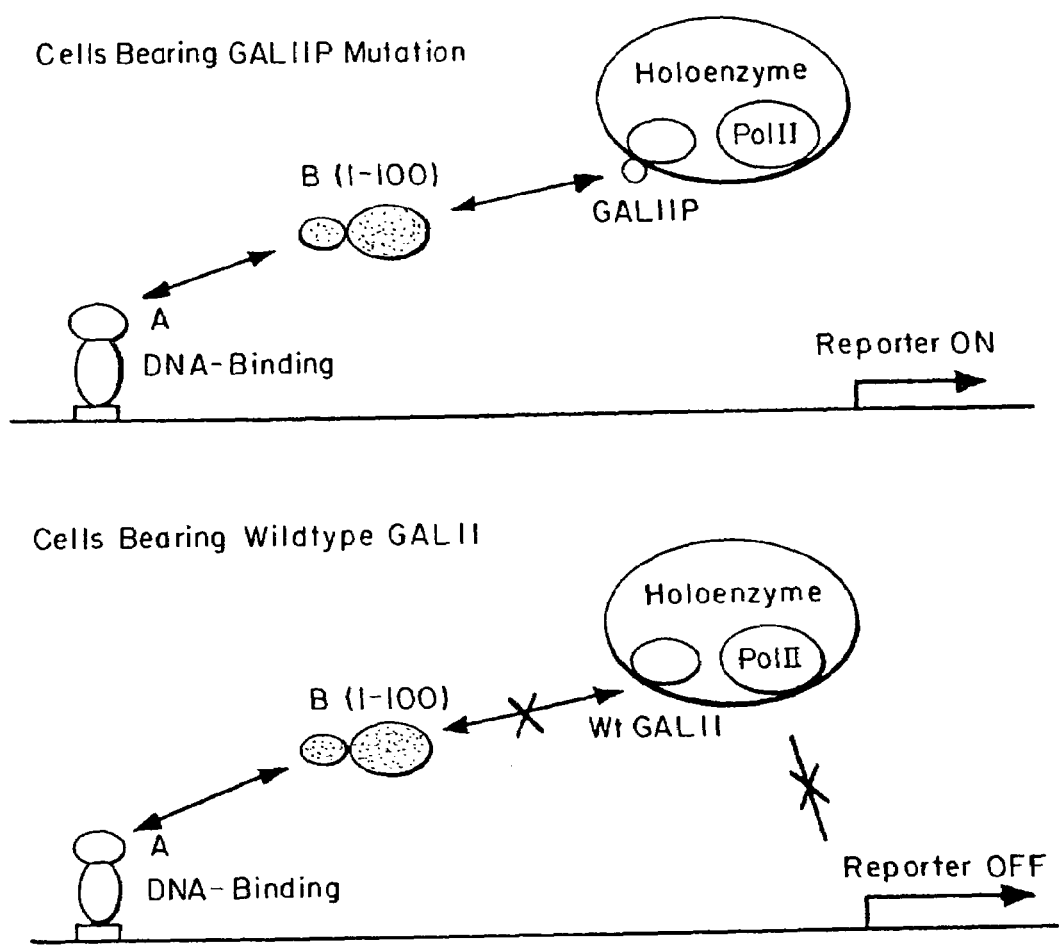

FIG. 9 is a schematic of the "three-component" protein—protein interaction transcriptional activation assay.

DESCRIPTION OF PREFERRED EMBODIMENTS

Novel Transcriptional Activators

Typical naturally-occurring transcriptional activators are modular proteins that have separable DNA binding and transcriptional activation regions (Ptashne, *Nature* 335:983, 1988). The present invention provides novel transcriptional activators, comprising a DNA binding moiety linked to a short, substantially hydrophobic peptide. The peptide is approximately 6–25 amino acids in length, and preferably is about 8–17 amino acids long. In particularly preferred embodiments, the peptide is 13 amino acids long.

The activating peptides of the present invention have amino acid sequences that do not correspond to a portion of a known transcriptional activation domain. Sequences of known transcriptional activation domains are available in the literature and in computer databases such as, for example, GenBank, PIR, SwissProt, NCBI, Prosite. One of ordinary skill in the art can therefore readily determine whether a particular peptide corresponds to a portion of a known activating region.

Preferred peptides of the present invention include at least approximately 25%, preferably at least approximately 50%, hydrophobic amino acids. That is, at least approximately 25–50% of the amino acid residues in preferred peptides of the present invention are alanine (A), leucine (L), isoleucine (I), valine (V), proline (P), phenylalanine (F), tryptophan (W), or methionine (M). Alternatively or additionally, preferred peptides include at least one aromatic residue (i.e., F, W, or tyrosine (Y)). Particularly preferred peptides also do not include any positively charged residues, at least not near the terminus farthest from the DNA-binding domain.

Particularly preferred peptides of the present invention are presented in Table 1 (identified with "LS"). Of the peptides presented in Table 1, those that, when expressed in yeast cells, activate β-galactosidase activity to at least about ½ the level observed with full-length Gal4 are preferred transcriptional activation peptides according tot he present invention. For example, peptides LS4 (QLPPWL; SEQ ID NO: 8); LS8 (QFLDAL; SEQ ID NO: 16); LS11 (LDSFYV; SEQ ID NO: 21); LS12 (PPPPWP; SEQ ID NO: 23); LS17 (SWFDVE; SEQ ID NO: 33); LS19 (QLPDLF; SEQ ID NO: 37); LS20 (PLPDLF; SEQ ID NO: 39); LS21 (FESDDI; SEQ ID NO: 41); LS24 (QYDLFP; SEQ ID NO: 45); LS25 (LPDLIL; SEQ ID NO: 47); LS30 (LPDFDP; SEQ ID NO: 55); LS35 (LFPYSL; SEQ ID NO: 57); LS51 (FDPFNQ; SEQ ID NO: 71); LS64 (DFDVLL; SEQ ID NO: 85); LS102 (HPPPPI; SEQ ID NO: 92); LS105 (LPGCFF; SEQ ID NO: 95); LS106 (QYDLFD; SEQ ID NO: 97); LS120 (YPPPPF; SEQ ID NO: 115); LS123 (PLPPFL; SEQ ID NO: 118); LS135 (LPPPWL; SEQ ID NO: 136); LS136 (VWPPAV; SEQ ID NO: 138); LS152 (DPPWYL; SEQ ID NO: 154); LS153 (LY; SEQ ID NO: 156); LS158 (FDPFGL; SEQ ID NO: 160); LS160 (PPSVNL; SEQ ID NO: 162); LS201 (YLLPTCIP; SEQ ID NO: 167); LS202 (LQVHNST; SEQ ID NO: 169); LS203 (VLDFTPFL; SEQ ID NO: 171); LS206 (HHAFYEIP; SEQ ID NO: 175); LS212 (PWYPTPYL; SEQ ID NO: 183); LS223 (YLLPFLPY; SEQ ID NO: 195); LS225 (YFLPLLST; SEQ ID NO: 199); LS232 (FSPTFWAF; SEQ ID NO: 209); LS241 (LIMNWPTY; SEQ ID NO: 221) are preferred inventive peptides. Particularly preferred are those that activate at least approximately as well as does full-length Gal4 (e.g., LS4, LS11, LS12, LS17, LS19, LS20, LS35, LS64, LS102, LS123, LS135, LS136, LS160, LS201, LS206, LS223, LS225 AND LS203).

The peptides of the present invention can be linked to any available DNA binding moiety to create a transcriptional activator of the present invention. For example, the peptides can be linked to a DNA-binding polypeptide (e.g., an intact protein that does not function as a transcriptional activator but binds to DNA, or any portion of a DNA-binding protein that retains DNA-binding activity) (see, for example, Nelson, *Curr. Op. Genet. Dev.* 5:180, 1995), a DNA-binding peptide derivative (see, for example, Wade et al., *JACS* 114:8784, 1992; Mrksich et al., *Proc. Natl. Acad. Sci. USA* 89:7586, 1992; Mrksich et al., *JACS* 115:2572, 1993; Mrksich et al., *JACS* 116:7983, 1994), an anti-DNA antibody (see, for example, Stollar, *Faseb J.*, 8:337, 1994), a DNA intercalation compound (e.g., p-carboxy methidium, p-carboxy ethidium, acridine and ellipticine), a groove binder (e.g., netropsinm, distamycin, and actinomycin; see, for example, Waring et al., *J. Mol. Recog.* 7:109, 1994), or a nucleic acid capable of hybridizing, to form a duplex or a triplex, with a target DNA sequence (see, for example Gee et al., *Am. J. Med. Sci.* 304:366, 1992). Preferably, the peptides are linked to a sequence-specific DNA-binding moiety, so that they can be targeted to a selected DNA site from which to activate transcription.

Any available linkage (e.g., covalent bonding, hydrogen bonding, hydrophobic association, etc.) may be utilized to associate the peptide to a DNA binding moiety, so long as the DNA-binding activity of the DNA-binding moiety and the transcriptional activation activity of the peptide are preserved. The linkage between the activating peptide and the DNA binding domain may be direct or may alternatively be mediated by a "linkage factor". A linkage factor is any entity capable of mediating a specific association between the DNA binding moiety and the activating peptide while preserving the activities of both. The term "specific association" has its usual meaning in the art: an association that occurs even in the presence of competing non-specific associations. The concept of linkage factors is known in the field of transcriptional activation and its scope and significance will readily be appreciated by those of ordinary skill in the art. To name but one example, rapamycin acts as a linkage factor when it mediates interactions between a DNA binding moiety that includes, for example, FK506 binding protein and a transcriptional activating moiety that includes a cyclophilin (Belshaw et al., *Proc. Natl. Acad. Sci. USA* 93:4604, 1996).

Preferred transcriptional activators of the present invention comprise a small, substantially hydrophobic peptide as described above, linked to a DNA-binding polypeptide that preferably has sequence-specific DNA binding activity. In particularly preferred embodiments, the peptide is linked to the DNA binding domain (i.e., a sufficient portion of the protein to recognize DNA but not to have transcriptional regulatory activity in the absence of the attached peptide) of a transcriptional regulatory protein (see, for example, Klug, *Ann. NY Acad. Sci.* 758:143, 1995). The choice of DNA binding domain will of course depend on the gene intended to be activated; the DNA binding domain should recognize a site positioned relative to the transcriptional start site of the gene that the activator can affect transcription. Preferably, the site should be within approximately 250–1000 basepairs of the transcription start site, although this is not strictly required as, particularly in higher mammalian systems (e.g., human), transcriptional activators are known to be effective when bound several thousand basepairs away (upstream or downstream) of the transcription start site (see, for example, Serneza, *Hum. Mutat.* 3:180, 1994; Hill et al. *Cell* 80:199, 1995).

The transcriptional activators of the present invention may be prepared by any available methods including, for example, recombinant nucleic acid methodologies (see, for example, Sambrook et al., *Molecular Cloning: a Laboratory Manual,* 2nd Ed., Cold Spring Harbor Press, Cold Spring Harbor, N.Y., 1989; Innis et al., *PCR Protocols: A Guide to Methods and Applications*, Academic Press, San Diego, Calif., 1990; Erlich et al., *PCR Technology: Principles and Applications for DNA Amplification*, Stockton Press, New York, N.Y., 1989, each of which is incorporated herein by reference), synthetic chemistry (see, for example, Bodansky et al., *The Practice of Peptide Synthesis*, Springer-Verlag, New York, N.Y., 1984; Atherton et al., *Solid Phase Peptide Synthesis: a Practical Approach*, IRL Press at Oxford University, England, 1989, each of which is incorporated herein by reference), or other techniques capable of linking the desired moieties to one another.

As described in Example 1, we prepared our transcriptional activators by using PCR to link random oligonucleotides, either 18 or 24 nucleotides long, to DNA encoding the Gal4 DNA binding domain, so that hybrid genes were produced that encoded a fusion protein consisting of a Gal4 DNA binding domain and either a 6-mer or 8-mer peptide. The hybrid genes were under control of a yeast promoter, so that the fusion proteins were expressed in yeast. We screened this library of potential transcriptional activators for those that could stimulate transcription of a β-galactosidase reporter gene that had upstream Gal4 binding sites, and also compared the activators' activity to that of full-length Gal4. After screening fewer than approximately 200,000 colonies, we had identified close to 200 activators. Thus, at least about 0.1% of our hybrid genes resulted in fusion proteins with transcriptional activation activity; about 5% of these activators stimulated transcription more effectively that did full-length Gal4 (see Table 1). Particularly preferred transcriptional activators of the present invention, therefore, activate transcription at least as effectively as does a known activating region linked to the same DNA binding moiety as is employed in the novel transcriptional activator. Such transcriptional activators, that effectively stimulate transcription through an activation domain only approximately 6–8 amino acids long, have not previously been described.

We further characterized our new transcriptional activators by determining the nucleotide sequence of their hybrid genes, and deducing therefrom the amino acid sequence of the encoded proteins (see Example 1). Although we found no obvious consensus sequence among our activator peptides, we noticed that all were substantially hydrophobic. Specifically, each of the peptides had at least about 30% hydrophobic residues. The least hydrophobic peptides, LS106 and LS202, had 33% and 29% hydrophobic residues; the most hydrophobic had 100% hydrophobic residues (LS123, LS135, LS136, LS235). Overall, of 109 peptides sequenced, a total of 682 residues were analyzed, 466 of which (68%) were hydrophobic. Also, approximately 90% of the peptides we analyzed included at least one aromatic residue. Only one peptide LS215, had a basic residue. LS215 is one of the weaker activators we identified.

We have observed that certain residues of the Gal4 DNA binding domain to which our peptides are linked contribute to the observed transcriptional activation (see Examples 1 and 2). Specifically, we have found that, for at least the LS201 activator, deletion of any one of the last five residues (residues 96–100) of the Gal4 DNA binding domain reduces activation activity about 10–1000 fold. Furthermore, substitution of either Phe97 or Val98 with Ala also reduces transcriptional activation about 40–150 fold. On the other hand, substitution of either Gln99 or Asp100 with Val has no effect on transcriptional activation. Also, Gal4 residues outside of 96–100 are not required for transcriptional activation (see Example 2).

The results presented in Example 2 demonstrate that the present invention actually describes three different set of activator peptides: i) those listed in Table 1; ii) peptides having an amino acid sequence identical to those listed in Table 1 except also including Gal4 DNA binding domain residues 96–100 (or 97–100); and iii) peptides having an amino acid sequence identical to those of set ii except that one or both of Gln99 and Asp100 has been substituted with another amino acid, preferably an Ala. Of these three sets, preferred activator peptides are those that stimulate transcription at least half as effectively as does full-length Gal4 in a side-by-side comparison, as described herein. Particularly preferred peptide activators of the present invention consist of Gal4 residues 96–100 (with or without substitutions at residues 99 and/or 100) plus either 6 or 8 additional, primarily hydrophobic residues. Accordingly, particularly preferred peptide activators are 11 or 13 amino acids long. Most preferred are 11- or 13-amino acid residues formed by linking one of the Table 1 peptides to Gal4 residues 96–100.

In order to further characterize our novel transcriptional activators, we assayed their ability to squelch activation by other transcriptional activators. A variety of natural activators, including a subset of mammalian transcriptional activators, have been observed to squelch transcriptional activation by Gal4 and Gcn4 when these natural activators are expressed in yeast (see, for example, Gill et al., *Nature* 334:721, 1988). Many of these activators have several acidic residues and have been called "acidic" transcriptional activators (see, for example, Ma et al., *Cell* 51:113, 1987). For the purposes of the present application, we define an "acidic transcriptional activator" as any activator that, when expressed in yeast, squelches activation by Gal4 and/or Gcn4. The squelching phenomenon is believed to result from competition by the activators (i.e., the test activator and Gal4 or Gcn4) for the same interaction target. If this model is correct, our data indicate that our novel transcriptional activators do not interact with the same target as do these acidic activators. Specifically, our new activators do not squelch activation by Gal4 (see Example 1).

As described in Example 1, we assayed the ability of our new transcriptional activators to squelch Gal4 activation by over-expressing the activators in a yeast cell. The specific method we employed is only one of many possible ways to overexpress a protein in yeast. In general, over-expression of transcriptional activators in yeast can be accomplished, for example, by introducing the activator gene into the cells on a high copy-number plasmid such as a 2μ vector. Alternatively or additionally, the activator gene can be introduced into the cell after being linked to a promoter that naturally directs, can be induced to direct, high levels of transcription in yeast. Exemplary high-expression promoters include Gal1/10, Adh, actin, etc.

Furthermore, similar squelching assays can be designed and performed to detect the ability of our transcriptional activators to interfere with the activity of any known transcriptional activator, in any desired experimental system. For example, we have tested our activators for their ability to squelch activation by Gal11, a protein that, when recruited to DNA through linkage to a DNA binding moiety, activates transcription as effectively as any known activator but does so through a mechanism distinct from that of the acidic activators and does not squelch their activity (see Barberis et al., Cell 81:359, 1995, incorporated herein by reference). As shown in Example 1, our new transcriptional activators do not squelch Gal11 activation. Thus, the present invention provides a novel class of transcriptional activators, unique in structure, activity characteristics, and method of identification. Each of these unique aspects is encompassed by the present invention.

We have also assayed the ability of our activator peptides to stimulate transcription in vitro. As described in Example 3, we find that an activator consisting of the Gal4 DNA binding domain (1–100) linked to peptide LS201 stimulates transcription in a yeast nuclear extract, and also appears to stimulate transcription in the presence of only the yeast holoenzyme. These findings lend support to our hypothesis that the present peptide activators constitute a novel class of transcriptional regulators that interact directly with the general transcription machinery.

One of ordinary skill in the art will readily appreciate that we have performed our transcriptional activator screen, and many of our analyses, in yeast primarily because of the simplicity of the system, and the demonstrated usefulness of information obtained from a yeast system in understanding mammalian, and particularly human, transcription. Many yeast transcriptional activators also function in higher systems, including human, and vice versa. The above-described screen for transcriptional activators can readily be repeated in other systems (e.g., in mammalian cells, preferably human cells), by selecting reporter constructs that are expressed in the desired cell type, and by inserting the hybrid gene library into an appropriate expression vector (that is, into a vector that directs protein in the desired cell type) (see Example 4). Suitable expression vectors and reporter genes for a wide array of systems are well known in the art.

The novel transcriptional activators described herein are particularly useful for introduction into cells to stimulate transcription therein since these new activators, even when over-expressed, do not interfere with transcriptional activation by classical activators such as the acidic activators. These activators are therefore highly useful for all applications involving controlled gene activation.

The novel transcriptional activators of the present invention can be delivered to cells by any of a variety of available techniques. For example, where the DNA binding moiety consists of a polypeptide, the transcriptional activator can be delivered to the cells in the form of a gene linked to a promoter that is expressed in the cells. Techniques for gene delivery to cells are well known in the art and include transformation, transfection, electroporation, infection, etc. Where the DNA binding moiety does not constitute a polypeptide, or where the transcriptional activator is delivered to cells as an intact protein, the transcriptional activator can be delivered by means of known drug delivery systems such as lipid micelles, or any other available technique.

Particularly preferred uses of the transcriptional activators of the present invention are in gene therapy. Specifically, many diseases are known or proposed either to be caused by reduced expression of a particular gene, or to be alleviated by increased expression of a particular gene. For example, diabetes results from reduced expression of insulin, and many cancers are caused by mutation of tumor-suppressor genes. Many other diseases (including, e.g., cystic fibrosis) can also be treated be gene therapy. The present transcriptional activators can be employed to treat such diseases. Specifically, a transcriptionally activating peptide of the present invention is linked to a DNA binding domain that recognizes a site appropriately located relative to the relevant gene so that the activator is effective when bound to the site. The activator is then delivered to appropriate cells by any available technique and is allowed to stimulate gene transcription. If desired, the activator can be provided to the cell as a gene under the control of a regulated promoter, so that expression of the activator in the cells can be controlled by exposure to an inducing agent. Such inducible promoters are well known in many systems. For example, useful human promoters include the glucocorticoid promoter, the NFκB promoter, the tetracycline promoter, or any other agent-responsive promoter. In one embodiment, the activator binding site is linked to a normal copy of a gene that is mutated in the cell. For example, where disruption of a gene results in a disease phenotype that is alleviated by introduction of a normal copy of the gene into the cell, the normal copy of the gene can be linked to a binding site for one of out activators and introduced into the cell along with the activator.

The present invention therefore encompasses methods of activating transcription by providing a novel transcriptional activator to a cell and recruiting that activator to a promoter at which it activates transcription. In preferred embodiments of the invention, the activator is recruited to the DNA by virtue of its being covalently attached to a DNA binding domain. However, it is also possible that mere expression of the activating peptides of the present invention in a target cell will activate transcription if the activating peptides themselves have the ability to interact both with a target in the transcription machinery and with another factor that recruits them to the DNA.

By providing novel transcriptional activators, the present invention also provides methods of identifying factors that interact with these activators, for example by standard biochemical, immunological, and/or genetic methods, or by the improved methods described herein. Once an interaction partner (or partners) is identified, that partner can be used in similar interaction-type assays to identify additional novel transcriptional activators of the type described herein.

System for Identifying Protein—Protein Interactions

In addition to providing novel transcriptional activators and associated methods of production and use, the present invention provides improved transcriptional activation systems for identifying and analyzing protein—protein interactions. As mentioned above, transcriptional activation systems have for several years been recognized as useful means for identifying interacting protein pairs. Such systems are often referred to as "two-hybrid" (see, for example Fields et al., Nature 340:245, 1989) or "interaction trap" (see, for example, Gyuris et al., Cell 75:791, 1993) assays.

The basic idea of these protein—protein interaction systems is exemplified in FIG. 7. A first protein or protein portion (protein A in FIG. 7), that does not itself stimulate transcription, is fused to a known DNA binding domain and the fusion product is expressed in a cell. The cell also contains a reporter construct in which the recognition site for the DNA biding domain is linked to a detectable reporter gene. A second fusion protein, in which a protein or protein portion that interacts with protein A (protein B in FIG. 7) is fused to a transcriptional activation domain, is also expressed in the cell. Interaction between protein A and protein B recruits the transcriptional activation domain to the DNA so that transcription of the reporter construct is induced.

These protein—protein interaction systems have been used to identify interaction partners for known proteins by fusing the known protein to either the DNA binding domain or the transcriptional activation domain and introducing the resulting fusion into cells along with a library fused to the other of the activation domain and the DNA binding domain. Typically, such assays are performed in yeast systems, with either β-galactosidase or a selectable marker (or both) as the reporter gene, but analogous systems have been developed in other cell types (see, for example, Vasavada et al., *Proc. Natl. Acad. Sci. USA* 88:10686, 1991; Fearon et al., *Proc. Natl. Acad. Sci. USA* 89:7958, 1992; Finkel et al., *J. Biol. Chem.* 268:5, 1993, each of which is incorporated herein by reference).

Many interacting protein pairs have been identified through the application of such systems (for reviews, see Fields et al., *Trends Genet.* 10:286, 1994; Allen et al., *Trends Biol. Sci.* 20:511, 1995, each of which is incorporated herein by reference), and standardized protocols can be found in readily available textbooks (see, for example, Shirley et al., *Methods Cell Biol.* 49:401, 1995, incorporated herein by reference).

Despite the success that has been achieved with known protein—protein interaction systems that rely on transcriptional activation, important drawbacks of the systems have also been identified (for discussions of drawbacks in reviews, see Fields et al., supra; Allen et al., supra). False positives are common. Moreover, these systems typically cannot be used to identify the interaction targets of transcriptional activators. Quite simply, if the activator is fused to the DNA binding moiety, the fusion activates transcription and the screen cannot be performed; if the activator is supplied as an activation domain, the assay typically still cannot identify interaction targets because the activator often cannot interact simultaneously with a DNA-bound version of its target and its target in the transcriptional machinery. Thus, interaction of the activator with its DNA-bound target precludes recruitment of the transcriptional machinery.

The present invention provides improved transcriptional activation systems for identifying protein—protein interactions. FIG. 8 presents one embodiment of an improved transcriptional activation of the present invention. The improvement depicted in FIG. 8 is that Gal11 is employed as the activator in a standard interaction trap or di-hybrid fusion assay. Thus, the target protein depicted in FIG. 8 is preferably not a transcriptional activator (or other component of the transcription machinery that, when recruited to DNA through linkage with a DNA binding domain, activates transcription.

In the system presented in FIG. 8, the DNA binding domain can be any DNA binding moiety that recognizes a known DNA sequence, but preferably corresponds to or includes a DNA binding domain of a known protein, most preferably of a transcriptional regulator for review, see Nelson, *Curr. Op. Genet. Dev.* 5:180, 1995. The most preferred DNA binding domains for use in these assays are the Gal4 (at least 1–100) and LexA(1–202) DNA binding domains.

The reporter gene utilized in the system of FIG. 8 can be any gene whose expression is readily detectable. In yeast systems, preferred reporters include the β-galactoside gene and selectable genes such as HIS3, LEU2, URA3, etc.; in human systems, the preferred reporter genes are those for SV40 large T antigen used in CV-1 cells; Vasvada et al., *Proc. Natl. Acad. Sci. USA* 88:10686, 1991), CD4, cell-surface molecules that can be selected in a cell sorter, or drug-selectable markers (Fearon et al., *Proc. Natl. Acad. Sci. USA* 89:7958, 1992).

Use of Gal11 as the activation domain in protein—protein interaction systems has many advantages over existing approaches. First of all, Gal11 is the most powerful known yeast activation domain (Himmelfarb et al., *Cell* 43:1299, 1990, incorporated herein by reference). Thus, assays employing Gal11 are likely to be even more sensitive than are existing systems and therefore to be useful for detecting weaker protein—protein interactions than are currently observed.

Furthermore, Gal11 does not squelch activation by known acidic activators, even when it is expressed at high levels (Barberis et al., *Cell* 81:359, 1995, incorporated herein by reference). Use of Gal11 in the transcriptional activation systems described herein therefore avoids toxicity problems often associated with over-expression of strong transcriptional activators.

Without wishing to be bound by any particular theory, we propose that Gal11 does not squelch transcriptional activation by acidic activators because it activates transcription through a different mechanism than that employed by the acidic activators. Specifically, we propose that Gal11 is part of the yeast RNA polymerase II holoenzyme and activates transcription when it is recruited to DNA simply because it, in turn, recruits the rest of the transcriptional machinery (see Barberis et al., supra). The present invention therefore encompasses the finding that use of RNA polymerase II holoenzyme components as transcriptional activation domains improves protein—protein interaction systems that assay for transcriptional activation.

Any component of the RNA polymerase II holoenzyme, or any artificial sequence that interacts with the holoenzyme, can be tested for its ability to be used as the transcriptional activation domain in the improved protein—protein interaction systems of the present invention depicted in FIG. 8. Recognizing that the literature includes differing descriptions of the RNA polymerase II holoenzyme, we define a "holoenzyme component" for the present purposes as any factor associated with the holoenzyme in a holoenzyme preparation that, when used in an in vitro transcription assay, responds to addition of purified transcriptional activator (e.g. Gal4; see, for example, Koleske et al. *Nature,* 368:466, 1994).

As mentioned above, one of the advantages of using Gal11 or another component of the RNA polymerase II holoenzyme as the transcriptional activation domain in a protein—protein interaction assay of the type described herein is that such factors do not squelch other known activators. In light of this teaching, one of ordinary skill in the art will recognize that other transcriptional activators that do not squelch acidic activators, even though the other activators are not components of the RNA polymerase II holoenzyme, are useful in the improved transcriptional activation systems of the present invention. For example, the novel transcriptional activators described above can be employed in the transcriptional activation systems described herein.

FIG. 9 presents another embodiment of an improved transcriptional activation system of the present invention, which embodiment we term the "three-component" system. In the three-component system of the present invention, a test protein is fused either to a non-Gal4 DNA binding domain or to Gal4(1–100), and an interaction target (e.g., a library) is fused to the other. Both fusion constructs are introduced into yeast cells carrying a mutant Gal11 that has gained the ability to interact with Gal4(1–100), and also carrying a reporter gene linked to the DNA binding site for the non-Gal4 DNA binding domain. Preferred embodiments employ the Gal11P allele (Himmelfarb et al., Cell 63:1299, 1990).

The Gal11P allele was first identified as a mutation that potentiated the activity of weak Gal4 derivatives (Himmelfarb et al., Cell 63:1209, 1990). We have since found that Gal11P is a gain-of-function mutation that confers onto Gal11 the ability to interact with the Gal4 dimerization domain found in Gal4(1–100) (Barberis et al., Cell 81, 359, 1995). Thus, in preferred embodiments of the three-component system of the present invention, interaction between the selected protein and its target recruits Gal4(1–100) to the DNA. Interaction between Gal11P and Gal4(1–100) then recruits the RNA polymerase II holoenzyme, thereby stimulating gene transcription (see Example 5). The affinity of the selected protein for its target correlates at least roughly with the observed level of transcriptional activation (see Example 5; see also Estojak et al., Mol. Cell. Biol. 15:5820, 1995, Yibing Wu, Ph.D. dissertation, Harvard University, 1996, incorporated herein by reference).

The three-component system of the present invention does not require use of the Gal11P allele per se. For example, the original Gal11P mutant bore an Ile residue at position 342 (Himmelfarb et al., Cell 63:1299, 1990). Subsequent randomization of codon 342 revealed that substitution with other hydrophobic residues (e.g., Leu or Val, to a lesser extent Met or Thr) yields the Gal11P phenotype to different extents (Barberis et al., Cell 81:359, 1995). Any of these Gal11 derivatives is useful in the practice of the present invention. Furthermore, the general principle observed is readily generalizable. That is, the present invention teaches an improved protein—protein interaction system employing an RNA polymerase II holoenzyme component gain-of-function mutation where the gain of function comprises an ability to interact with a component to which other entities can be fused for the performance of a three-component screen as described herein. Any other appropriate holoenzyme component mutant could readily be employed in the practice of the present invention.

The three-component system of the present invention has many advantages over existing protein—protein interaction systems. The primary advantage is that use of the mutant holoenzyme component (e.g., Gal11P) system provides a straightforward control that can be used to distinguish "true" positives, that rely on recruitment of the transcription machinery to the promoter, from "false" positives produced sporadically by the system. For example, in a screen in which a selected protein (e.g., a transcriptional activator) is linked to Gal4(1–100) and a library is linked to the DNA binding moiety, "positive" library clones (i.e., those that encode a true interaction partner to the selected protein) are identified as those that result in transcriptional activation in a Gal11P cell but not in a Gal11 cell. Better yet, the screen is performed in a Gal11 cell that also contains the Gal11P gene under the control of a regulatable promoter. The screen is performed under conditions in which the Gal11P gene is expressed (since Gal11P is a dominant mutation, this expression effectively converts the cell to a Gal11P cell), and then the same colonies are tested under conditions in which the Gal11P gene is not expressed. This strategy avoids the complication of having to isolate plasmids from individual Gal11P colonies transform them into Gal11 cells and re-test the new transformants.

Also, because the transcriptional activation in this system is via the "Gal11" mechanism, over-expression of the selected protein-Gal4(1–100) fusion will not squelch endogenous activators. Furthermore, in preferred embodiments of this three-component system, where the selected protein fused to Gal4(1–100) is a transcriptional activator, the system offers an additional built-in advantage. Specifically, the integrity of the Gal4(1–100) fusion can readily be tested by providing the cell with a second reporter construct, this one including Gal4 DNA binding sites, and detecting activation of that promoter by the fusion. One of ordinary skill in the art will readily recognize that this integrity control may be performed simultaneously with or separately from any protein—protein interaction screen. That is, the second reporter can be introduced into a cell with just the Gal4 (1–100) fusion, or with any or all of the other constructs used in the full screen.

Applications of the improved transcriptional activation systems described herein are, of course, not limited to the identification of new protein—protein interactions. As is known for the standard di-hybrid and interaction-trap systems, such assays can usefully be employed to test the existence or dissect the specifics of a protein—protein interaction (see, for example, Fields et al., Trends Genet. 10:286, 1994; Allen et al., Trends Bioch. Sci. 20:511, 1995). For example, the significance of mutations, deletions, or insertions in different regions of the interacting components can be assayed by studying their effects on transcriptional activation in these systems. Techniques for producing such mutations, deletions, and insertions are well known in the art. The advantages described herein of being able to examine the significance of effects, for example by comparing results in Gal11P and Gal11 cells, are equally applicable to these types of assays.

Other Embodiments

One of ordinary skill in the art will readily recognize that the foregoing represents merely a detailed description of certain preferred embodiments of the present invention. Various modifications and alterations of the compositions and methods described above can readily be achieved using expertise available in the art, and are within the scope of the following claims.

For example, as mentioned above, all of the assays described herein can be performed in any of a variety of cell types. Yeast cells are often selected as the most convenient for experimental manipulation, but even there, the variety of yeast strains that are available affords a wide range of opportunity for the practice of the present invention.

In some instances, it may be desirable to perform the assays of the present invention in cells whose capacity for transcriptional activation has been altered. For example, we have identified various dominant mutations in the yeast TBP protein that enhance the transcriptional activation potential of various yeast activators (see Example 6). Specifically, the N69R and V71R mutations of yeast TBP, when expressed from an ARS-CEN plasmid in otherwise wild type yeast, increase the observed transcriptional activity of G4RII' derivatives by 2–3 fold, and that of a Gal4-Gal11 fusion (form a site 1200 basepairs upstream of the transcription start) 12 fold. Use of such mutant TBPs in the assays described above may make the system more sensitive.

EXAMPLES

Example 1

Identification and Characterization of Novel Transcriptional Activators

Materials and Methods

MEDIA, YEAST STRAINS, AND REPORTER/PLASMIDS: Rich (YPD) and synthetic complete (SC) yeast media were prepared as described (Rose et al., *Methods in Yeast Genetics*, Cold Spring Harbor Press, Cold Spring Harbor, N.Y., 1990, incorporated herein by reference). Yeast strain JPY9 was described in Wu et al., *EMBO J.* 1996. The genotype of JPY9 is MATα; ura3-52, trp1Δ63, leu2Δ1, his3Δ200, lys2Δ385, gal4Δ11, gal80. Yeast reporter plasmids pRY131Δ2μ, pRJR227, and pJP169 contain the reporter gene, lacZ, and various upstream activating sites: UASg of GAL-lacZ, five consensus 17mer GAL4 binding sites, and two LexA binding sites, respectively. These upstream activating sites are all 191 bp away from the TATA box (Yocum et al., *Mol. Cell. Biol.* 4:1985, 1984; Carey et al., *Science* 247:710, 1990). Reporter plasmids were integrated at the URA3 locus of yeast after ApaI digestion.

LIBRARY CONSTRUCTION: The following oligonucleotides were synthesized: oligo1 has 30 nucleotides paring the upstream of coding sequence of GAL4(1–100) in plasmid pRJR217 (Wu et al., *EMBO J.*, 1996); oligo2 contains 30 nucleotides paring downstream of GAL4(1–100) coding sequence, a stop codon, 24 random nucleotides, and 18 nucleotides paring the C-terminus of GAL4(1–100) coding sequence; oligo3 contains 30 bp paring the downstream of GAL4(1–100) coding sequence, a stop codon, 18 random nucleotides, and 18 nucleotides paring the C-terminus of GAL4(1–100+840–850) coding sequence. DNA fragments encoding GAL4(1–100)+X8 or GAL4(1–100+840–850)+X6 were then generated by PCR using primer pairs oligo1–2 and oligo1–3, respectively, and using plasmid DNA RJR217 encoding GAL4(100), and pRJR206 encoding GAL4 (1–100+840–850), respectively, as template. These PCR fragments were co-transformed into S. cerevisiae strain JPY9::RJR227 using LiOAc method (Rose et al. supra 1990) along with a yeast expression vector, pRJR217, that was linearized with NcoI and SalI. The PCR fragments were integrated into the vector by homologous recombination (Lehming et al., supra 1995), yielding a library of yeast colonies.

ACTIVATION ASSAY: The yeast colonies, 2–3 days after transformation, were subject to X-gal filter assay (Rose et al., supra 1990). Blue colonies were selected, plasmids were rescued from these colonies and re-transformed into yeast strain JPY9:RJR227 and JPY9:RY131Δ2μ. β-galactosidase activities were then determined by X-gal filter assay and ONPG liquid assay (Rose et al., supra 1990).

SQUELCHING ASSAY: The plasmids encoding the activating peptides were transformed into the yeast strain YPY9:JP169 along with a plasmid encoding lexA(1–87)-GAL4(74–881), or lexA(1–87)-GAL11(141–1081). Both activating peptides and lexA-GAL4 or lexA-GAL11 are in the plasmids, driven by the actin promoter. Both plasmids have the Ars-Cen replicating origin. Because the activating peptide gene and the lexA-fusion genes are under the control of the same promoter, they should be produced at the same level in yeast cells. The transformed cells were assayed for β-gal activity and compared with the cells that were transformed with lexA-GAL4 or lexA-GAL11 alone.

SEQUENCING: All plasmids encoding the activating peptides were sequenced using sequenase v2.0 kit from Amersham/USB.

ACTIVATION IN MAMMALIAN SYSTEM: The DNA encoding the yeast activating peptides was amplified by PCR and cloned into an mammalian expression vector, pcDNA3 (from Invitrogen). The resulting plasmids were co-transfected into HeLa cells along with a reporter plasmid pG5EC which encodes a chloroamphenicol acetyl transferase (CAT) gene driven by the minimal adenovirus E1b promoter bearing five upstream consensus 17 mers of GAL4 binding sites. The CAT activities were determined using [$^{14}$C] chloroamphenicol as substrate (Sambrook et al. Molecular Cloning: a Laboratory Manual, 2d Ed. Cold Spring Harbor Laboratory Press, Cold Spring Harbor, N.Y., 1989).

Results

We constructed expression libraries that would produce a Gal4 DNA binding domain (either 1–100 or 100+840–850) fused to short, randomized peptides (6 or 8 amino acid residues in length). We transformed these libraries into a yeast strain containing a reporter plasmid that included Gal4 DNA binding sites. One reporter plasmid (pRJR227) contained five Gal4 17-mers upstream of the β-galactosidase gene; another (p4131Δ2μ) contained a natural UAS$_G$ upstream of the same gene. We selected blue colonies by X-gal filter assay, recovered plasmids from the yeast cells in these blue colonies, and re-transformed and re-screened these positive plasmids. From approximately 200,000 colonies screened, we obtained approximately 200 activators. Transcriptional activation by each of these activators was dependent on the presence of Gal4 binding sites in the reporter construct, indicating that activation is specific. The activation potential varied among the activators (see Table 1); several (~5%) activated better than did full-length Gal4.

We determined the nucleotide sequence of the inserts in our positive clones, and thereby determined the amino acid sequence of the transcriptional activators (see Table 1). Although no obvious consensus sequence emerged, we found that our peptide activation domains contained primarily hydrophobic and acidic residues. No basic residues were observed, except in one weak activator. Each of our peptide sequences was new-in that, no peptide correspond to a known sequence in the SwissProt database.

TABLE 1

Activators from Random Library GAL 1–100 + 840–850 + X6

| Plasmid | Sequence | SEQ ID NO | Plate Assay | Liquid Assay (5X17 mers) β-gal Activity | Net Charge |
|---|---|---|---|---|---|
| RJR191 | GAL4 1–881 (Full length) | | +++ | 2350 | |
| RJR182 | GAL4 1–100 + 840–881 | | ++ | 1739 | |
| RJR217 | GAL4 1–100 | | − | 3 | |
| RJR206 | GAL4 1–100 + 840–850 (840 WTDQTAYNAFG 850) | 1 | ± | 41 | |
| LS1 | CCC CTC TTN NCN NCC CTC | 2 | | ++ | |

TABLE 1-continued

| | | | | | | | | | |
|---|---|---|---|---|---|---|---|---|---|
| LS2 | ATT | CCG | CCA | CCG | TAT | TTC | 3 | ++ | | 0 |
| | I | P | P | P | Y | F | 4 | | | |
| LS3 | CTG | CCC | GGG | TGT | TTC | TTC | 5 | ++ | | 0 |
| | L | P | G | C | F | F | 6 | | | |
| LS4 | CAG | CTC | CCC | CCC | TGG | TTA | 7 | ++ | 1882 | 0 |
| | Q | L | P | P | W | L | 8 | | | |
| LS5 | TAC | TGG | CCC | TCC | CCC | TTC | 9 | ++ | | 0 |
| | Y | W | P | S | P | F | 10 | | | |
| LS6 | GAG | TTC | CCC | TAT | GAC | TTG | 11 | + | | -2 |
| | E | F | P | Y | D | L | 12 | | | |
| LS7 | ACC | GCC | GAA | TTC | CCC | CTC | 13 | ++ | | -1 |
| | T | A | E | F | P | L | 14 | | | |
| LS8 | CAA | TTT | CTA | GAC | GCA | CTT | 15 | + | 1174 | -1 |
| | Q | F | L | D | A | L | 16 | | | |
| LS9 | ACA | TTC | CCT | GAC | CCC | TTC | 17 | + | | -1 |
| | T | F | P | D | P | F | 18 | | | |
| LS10 | ATC | GGC | CCA | NCN | CTT | TTC | 19 | ++ | | |
| LS11 | TTG | GAT | TTT | TCC | TAC | GTC | 20 | +++ | 2196 | -1 |
| | L | D | F | S | Y | V | 21 | | | |
| LS12 | CCC | CCA | CCA | CCC | TGG | CCC | 22 | +++ | 2109 | 0 |
| | P | P | P | P | W | P | 23 | | | |
| LS13 | CTC | TTT | GAA | TGA | GGA | ACC | 24 | + | | -1 |
| | L | F | E | * | | | 25 | | | |
| LS14 | CTG | CTC | GAC | ATA | CCT | TTC | 26 | ++ | | -1 |
| | L | L | D | T | 0 | F | 27 | | | |
| LS15 | CTC | CCC | GAC | GCC | TTT | CTC | 28 | ++ | | -1 |
| | L | P | D | A | F | L | 29 | | | |
| LS16 | CTC | TTC | CCC | GAC | CTC | AAC | 30 | ++ | | -1 |
| | L | F | P | D | L | N | 31 | | | |
| LS17 | TCT | TGG | TTT | GAT | GTC | GAA | 32 | ++ | 1961 | -2 |
| | S | W | F | D | V | E | 33 | | | |
| LS18 | CTT | GAA | CCT | CCG | CCC | TGG | 34 | ++ | | -1 |
| | L | E | P | P | P | W | 35 | | | |
| LS19 | CAG | CTA | CCT | GAT | CTG | TTC | 36 | +++ | 1727 | -1 |
| | Q | L | P | D | L | F | 37 | | | |
| LS20 | CCT | CTC | CCA | GAC | CTC | TTC | 38 | +++ | 2215 | -1 |
| | P | L | P | D | L | F | 39 | | | |
| LS21 | TTC | GAA | TTC | GAT | GAT | ATC | 40 | ++ | 9814 | -3 |
| | F | E | F | D | D | I | 41 | | | |
| LS22 | ACC | TTT | TTC | GAT | ACC | CCC | 42 | + | | -1 |
| | T | F | F | D | T | P | 43 | | | |
| LS24 | CAA | TAC | GAT | CTA | TTC | GAT | 44 | ++ | 1153 | -2 |
| | Q | Y | D | L | F | D | 45 | | | |
| LS25 | CTA | CCG | GAC | TTA | ATT | CTC | 46 | ++ | 1229 | -1 |
| | L | P | D | L | I | L | 47 | | | |
| LS26 | CCC | CCC | CTG | GAT | CCA | TGG | 48 | ++ | | -1 |
| | P | P | L | D | P | W | 49 | | | |
| LS27 | CAA | TAC | GAT | CTA | TTC | GAT | 50 | ++ | | -2 |
| | Q | Y | D | L | F | D | 51 | | | |
| LS28 | ACC | TTG | TGA | CGC | CAG | AGC | 52 | ++ | | 0 |
| | T | L | * | | | | 53 | | | |

TABLE 1-continued

| | | | | | |
|---|---|---|---|---|---|
| LS30 | CTA CCA GAC TTC GAT CCA<br>L   P   D   F   D   P | 54<br>55 | + | 886 | -2 |
| LS35 | CTA ATC CCA TAC TCC CTG<br>L   F   P   Y   S   L | 56<br>57 | ++ | 1825 | 0 |
| LS40 | TTT CCT GAC CTC TTC CCC<br>F   P   D   L   F   P | 58<br>59 | ++ | | -1 |
| LS41 | CCT AAC CCC TTC CCA CTG<br>P   N   P   F   P   L | 60<br>61 | ++ | | 0 |
| LS42 | TTC TAG AAC ACA CCC CCG<br>F   * | 62<br>63 | ± | | 0 |
| LS43 | CCC CCC CCC CAA TAT TTC<br>P   P   P   Q   Y   F | 64<br>65 | + | | 0 |
| LS44 | GAG GAC ACC CCC CCC TGG<br>E   D   T   P   P   W | 66<br>67 | ± | 552 | -2 |
| LS46 | TTC CCC CCC CCC CCA TTC<br>F   P   P   P   P   F | 68<br>69 | ++ | | 0 |
| LS51 | TTC CCC CCA TTC AAC CAA<br>F   P   P   F   N   Q | 70<br>71 | + | 950 | 0 |
| LS52 | CCC CTG TTC TGA CTC GGA<br>P   L   F   * | 72<br>73 | + | | 0 |
| LS53 | ACC GGT CCA CCA GAG CTA<br>T   G   P   P   E   L | 74<br>75 | + | | -1 |
| LS60 | CTA ATC CCA TAC TCC CTG<br>L   I   P   Y   S   L | 76<br>77 | + | | 0 |
| LS61 | ACC TTC CCT TAC TCA CTG<br>T   F   P   Y   S   L | 78<br>79 | ++ | | 0 |
| LS62 | GGC AGC TTC GAA CTC CTC<br>G   S   F   E   L   L | 80<br>81 | + | | -1 |
| LS63 | CTG GAA TAC CCC ACC ACC<br>L   E   Y   P   T   T | 82<br>83 | + | | -1 |
| LS64 | AAT TTT GAT GAC CTA CTC<br>N   F   D   D   L   L | 84<br>85 | +++ | 1905 | -2 |
| LS66 | CTG GAC GTA TTT TCA CAC<br>L   D   V   F   S   H | 86<br>87 | ++ | | -1 |
| LS101 | CAG CTA CCT GAT CTG TTC<br>Q   L   P   D   L   F | 88<br>89 | ++ | | -1 |
| LS102 | CAC CCC CCC CCT CCC ATT<br>H   P   P   P   P   I | 90<br>91 | ++ | 1158 | 0 |
| LS104 | CCC CTG TTC TGA CTC GGA<br>P   L   F   * | 92<br>93 | ++ | | 0 |
| LS105 | CTG CCC GGG TGT TTC TTC<br>L   P   G   C   F   F | 94<br>95 | ++ | 2403 | 0 |
| LS106 | CAA TAC GAT CTA TTC GAT<br>Q   Y   D   L   F   D | 96<br>97 | + | 1385 | -1 |
| LS107 | GCT CTC CCG CCG TAC CTC<br>A   L   P   P   Y   L | 98<br>99 | + | | 0 |
| LS108 | TTC CTC CCC TCC CTT CCC<br>F   L   P   S   L   P | 100<br>101 | ++ | | 0 |
| LS110 | ATC CCT CTC CTC TGT CTC<br>I   P   L   L   C   L | 102<br>103 | ± | 122 | 0 |
| LS111 | ATG CTC CCT CCC TAC ATC<br>M   L   P   P   Y   I | 104<br>105 | ++ | | 0 |

TABLE 1-continued

| | | | | |
|---|---|---|---|---|
| LS114 | CCC CCC TAC ATA TGG CCA<br>P P Y I W P | 106<br>107 | ++ | 0 |
| LS115 | GCG CTA TGG TAG CTA CCC<br>A L W * | 108<br>109 | ++ | 0 |
| LS118 | GAC CTC AAT ATT TTC TAG<br>D L N I F * | 110<br>111 | ++ | −1 |
| LS119 | CTA CCC ATG ACN CCG TTC<br>L P M T P F | 112<br>113 | + | 0 |
| LS120 | TAC CCC CCG CCG CCC TTT<br>Y P P P P F | 114<br>115 | + | 1443 | 0 |
| LS121 | NNN CCC GTA GNN CNC TGG | 116 | ++ | |
| LS123 | CCC CTT CCN CCT TTT CTT<br>P L P P F L | 117<br>118 | +++ | 1892 | 0 |
| LS125 | CTC CCC ACC ATG CCC CTC<br>L P T M P L | 119<br>120 | + | 0 |
| LS126 | CTC TTC CTA CCA CCC ACC<br>L F L P P T | 121<br>122 | + | 0 |
| LS129 | ACC GCC GAA TTC CCC CTC<br>T A E F P L | 123<br>124 | + | −1 |
| LS130 | ACC GAT TTC CTT CTG CTG<br>T D F L L L | 125<br>126 | ++ | −1 |
| LS131 | GGA GAA TAT TTC CCC TTC<br>G E Y F P F | 127<br>128 | ++ | 0 |
| LS132 | TTT ATA GAT CCC CCT CTC<br>F I D P P L | 129<br>130 | ++ | −1 |
| LS133 | CTA ATC CCA TAC TCC CTG<br>L I P Y S L | 131<br>132 | ++ | 0 |
| LS134 | CAA TAC GAT CTA TTC GAT<br>Q Y D L F D | 133<br>134 | ++ | −2 |
| LS135 | TTA CCT CCC CCC TGG CTT<br>L P P P W L | 135<br>136 | +++ | 3121 | 0 |
| LS136 | CTC TGG CCA CCT GCC GTA<br>V W P P A V | 137<br>138 | +++ | 1829 | 0 |
| LS140 | CCA ACA AAC TTC TAC TGA<br>P T N F Y * | 139<br>140 | + | 0 |
| LS142 | CTA ATC CCA TAC TTC CTG<br>L I P Y F L | 141<br>142 | + | 0 |
| LS147 | ATC TGC GAG AGT TTC TTT<br>I C E S F F | 143<br>144 | ++ | −1 |
| LS148 | GCG GAC CCG TGG CTA CTC<br>A D P W L L | 145<br>146 | ++ | −1 |
| LS149 | GCG CAG TAC CCT TTC TTC<br>A Q Y P F F | 147<br>148 | ++ | 0 |
| LS150 | CCT CCG TCA TTC TTC GGC<br>P P S F F G | 149<br>150 | ++ | 0 |
| LS151 | CTT TCC AGC CTT CCC TTC<br>P S S L P F | 151<br>152 | ++ | 0 |
| LS152 | GAC CCA CCA TGG TAC CTT<br>D P P W Y L | 153<br>154 | + | 1783 | −1 |
| LS153 | CTC TAC TAA TAA TAA GCA<br>L Y * | 155<br>156 | + | 1262 | 0 |
| LS155 | CCT ATC CCC GGT TTC ACT<br>P I P G F T | 157<br>158 | + | 0 |

TABLE 1-continued

| Plasmid | Sequence | | | | | | SEQ ID NO | Net Charge | β-gal Activity (in YAG6) X-gal | ONPG |
|---|---|---|---|---|---|---|---|---|---|---|
| LS158 | TTT<br>F | GAC<br>D | CCC<br>P | TTG<br>F | GGC<br>G | ATC<br>I | 159<br>160 | | + | 1856 | −1 |
| LS160 | CCC<br>P | CCC<br>P | AGT<br>S | GTG<br>V | AAC<br>H | CTC<br>L | 161<br>162 | | +++ | 2891 | 0 |
| LS161 | CCA<br>P | GAC<br>D | AAC<br>N | GTC<br>V | CTA<br>L | CCG<br>P | 163<br>164 | | ++ | | −1 |

Activators from Random Library GAL4 1–100 + X8

| Plasmid | Sequence | | | | | | SEQ ID NO | Net Charge | β-gal Activity (in YAG6) | |
|---|---|---|---|---|---|---|---|---|---|---|
| | | | | | | | | | X-gal | ONPG |
| RJR191 | GAL4 (1–881, Full length) | | | | | | | | +++ | 2804 |
| RJR217 | GAL4(1–100)<br>(89KALLTGLFVQD100) | | | | | | 165 | | − | 3 |
| LS201 | TAC<br>Y | CTT<br>L | TTA<br>L | CCA<br>P | ACC<br>T | TGT<br>C | ATA<br>I | CCT<br>P | 166<br>167 | 0 | ++++ | 4395 |
| LS202 | CTA<br>L | CAA<br>Q | GTC<br>V | CAC<br>H | AAC<br>N | AGC<br>S | AGA<br>T | TAG | 168<br>169 | 0 | ++ | 1655 |
| LS203 | GTT<br>V | CTT<br>L | GAC<br>D | TTC<br>F | ACC<br>T | CCT<br>P | TTC<br>F | CTC<br>L | 170<br>171 | −1 | ++ | 1128 |
| LS205 | CCC<br>P | CTT<br>L | ACC<br>T | TAC<br>Y | CCC<br>P | CTC<br>L | GCC<br>A | GGA<br>G | 172<br>173 | 0 | + | 325 |
| LS206 | CTC<br>L | CTC<br>L | GCC<br>A | TTT<br>F | TAC<br>Y | GAG<br>E | ATA<br>I | CCG<br>P | 174<br>175 | −1 | +++ | 1423 |
| LS207 | CCC<br>P | CCT<br>P | GAC<br>D | ACC<br>T | TAC<br>Y | ATC<br>I | TTC<br>F | TTA<br>F | 176<br>177 | −1 | + | |
| LS208 | CAA<br>Q | CTC<br>L | AAC<br>N | TAC<br>Y | CCA<br>P | CTC<br>L | GCC<br>A | ATA<br>I | 178<br>179 | 0 | + | 173 |
| LS209 | CTC<br>L | GTA<br>V | CTA<br>L | CCC<br>P | CAG<br>Q | CCG<br>P | CAA<br>Q | CTC<br>L | 180<br>181 | 0 | + | |
| LS212 | CCT<br>P | TGG<br>W | TAC<br>Y | CCT<br>P | ACG<br>T | CCG<br>P | TAT<br>Y | CTG<br>L | 182<br>183 | 0 | ++ | 811 |
| LS215 | TGG<br>W | CTC<br>L | CGA<br>R | TCG<br>S | TTC<br>F | AGC<br>S | GTT<br>V | CCC<br>P | 184<br>185 | +1 | ± | 187 |
| LS217 | CTT<br>L | GAA<br>E | CCA<br>P | TCA<br>S | CTA<br>L | TAT<br>Y | ATG<br>M | ATA<br>I | 186<br>187 | 0 | + | |
| LS218 | TGC<br>C | ATC<br>I | TTG<br>L | TCC<br>S | CAC<br>H | CAC<br>H | GCT<br>A | CCT<br>P | 188<br>189 | 0 | ± | |
| LS220 | GAC<br>D | CTC<br>L | ACA<br>T | TGC<br>C | TGT<br>C | TTT<br>F | TGC<br>C | CTC<br>L | 190<br>191 | −1 | + | 198 |
| LS221 | CCG<br>P | TTT<br>F | ATT<br>I | GGC<br>G | GGC<br>G | CCT<br>P | TAC<br>Y | GCA<br>A | 192<br>193 | 0 | + | |
| LS223 | TAC<br>Y | CTA<br>L | CTA<br>L | CCT<br>P | TTC<br>F | CTT<br>L | CCG<br>P | TAC<br>Y | 194<br>195 | 0 | +++ | 2366 |
| LS224 | TAC<br>Y | CCC<br>P | TGG<br>W | TTT<br>F | CCA<br>P | GTC<br>V | CCC<br>P | TTA<br>F | 196<br>197 | 0 | ± | |
| LS225 | TAT<br>Y | TTA<br>F | CTA<br>L | CCT<br>P | CTC<br>L | CTC<br>L | TCC<br>S | ACT<br>T | 198<br>199 | 0 | +++ | 2714 |
| LS226 | CTC<br>L | TCC<br>S | ATT<br>I | CAA<br>Q | CCC<br>P | TAT<br>Y | TTT<br>F | TTT<br>F | 200<br>201 | 0 | ± | |
| LS228 | GCC<br>A | CTA<br>L | TTC<br>F | TAC<br>Y | CTC<br>L | CTC<br>L | TAA<br>L* | AAG | 202<br>203 | 0 | + | 419 |

TABLE 1-continued

| | | | | | | | | | | |
|---|---|---|---|---|---|---|---|---|---|---|
| LS230 | CCN<br>P | TGG<br>W | CCC<br>P | TAC<br>Y | TAT<br>Y | TTN<br>F | CCG<br>P | ATC<br>I | 204<br>205 | 0 | + |
| LS231 | CCG<br>P | ATT<br>I | TGG<br>W | CAA<br>Q | TAT<br>Y | ACC<br>TI | ATT | TTC<br>F | 206<br>207 | 0 | + |
| LS232 | TTA<br>F | TCC<br>S | CCC<br>P | ACC<br>T | TTT<br>F | TGG<br>W | GCA<br>A | TTC<br>F | 208<br>209 | 0 | ++ |
| LS233 | GAC<br>D | CCC<br>P | CCC<br>P | TAC<br>Y | GCC<br>A | TAT<br>Y | ACT<br>T | CTG<br>L | 210<br>211 | -1 | + 126 |
| LS235 | CCT<br>P | GCA<br>A | CTC<br>L | CTG<br>L | TTT<br>F | CCA<br>P | TTC<br>F | ATC<br>I | 212<br>213 | 0 | + 763 |
| LS236 | TTC<br>F | ACC<br>T | TAC<br>Y | GCT<br>A | CTC<br>L | CCC<br>P | TTC<br>F | CCC<br>P | 214<br>215 | 0 | + 390 |
| LS239 | CTC<br>L | TTA<br>F | CCA<br>P | CTG<br>L | CCT<br>P | CTC<br>L | TTC<br>F | CTC<br>L | 216<br>217 | 0 | ± |
| LS240 | CTA<br>L | TTC<br>F | CCC<br>P | TGG<br>W | ACA<br>T | TAC<br>Y | CAA<br>Q | CTT<br>L | 218<br>219 | 0 | + |
| LS241 | CTT<br>L | ATT<br>T | ATG<br>M | AAC<br>N | TGG<br>W | CCT<br>P | ACA<br>T | TAT<br>Y | 220<br>221 | 0 | ++ |
| LS243 | TAT<br>Y | ATT<br>I | TTC<br>F | NCG<br>? | CTG<br>L | AGC<br>S | TTA<br>F | TCA<br>S | 222<br>223 | | |
| LS244 | CTA<br>L | ACA<br>T | CCC<br>P | CTC<br>L | CCC<br>P | TCA<br>S | TGG<br>W | CTA<br>L | 224<br>225 | 0 | + |

We investigated the importance of the hydrophobic and acidic residues in our peptide activation domains by performing site-directed mutagenesis on selected activators. In particular, we converted the I residue of activator LS201 to a R, and found that the formerly strong activator was converted to a weak one. This finding indicates that positive charge does not correlate with activation potential in our activators.

We also tested the importance of peptide sequence by scrambling the residues of the LS201 activator. As shown in FIG. 1, such scrambling reduces activation potential about 44–260 fold.

We also performed "squelching" assays (Gill et al., Nature 334:721, 1988) with our activators. Specifically, we tested whether over expression of our activators affected transcriptional activation directed by LexA-fused activators from a template containing 2 LexA binding sites 141 base pairs upstream of a Gal1-LacZ gene fusion (pJP168). Each of the activators tested squelched activation by other of our activators; however, none of our activators squelched activation by either lexA-Gal4 or lexA-Gal11 (see Table 3). This finding suggests that our new transcriptional activators act through a target distinct from that contacted by either Gal4 or Gal11. Without wishing to be bound by any particular theory, we propose that our novel transcriptional activators stimulate transcription by contacting surfaces in the RNA polymerase II holoenzyme that are not contacted by other, known transcriptional activators. Thus, these novel transcriptional activators can be introduced into cells without deleterious effects on natural transcription activation mechanisms at work in those cells.

TABLE 2

Activating Peptides do not Squelch Activation by LexA-Gal4 or LexA-Gal11

| Novel Activator | LexA-Gal4 Units of β-Galactosidase Activity | % Activation | LexA-Gal11 Units of β-Galactosidase Activity | % Activation |
|---|---|---|---|---|
| none | 3216 ± 241 | 100 | 3450 ± 200 | 100 |
| Gal4 | 520 ± 245 | 16 | 2504 ± 410 | 73 |
| LS64 | 3306 ± 758 | 103 | 4153 ± 515 | 120 |
| LS110 | 2785 ± 672 | 87 | 3518 ± 622 | 102 |
| LS160 | 3383 ± 782 | 105 | 3833 ± 842 | 111 |
| LS201 | 2842 ± 308 | 88 | 4288 ± 621 | 124 |

We investigated the role played by the DNA-binding domain residue immediately adjacent the peptide in our novel activators. Specifically, we deleted that residue, an aspartic acid, and tested the ability of the deletion derivatives to activate transcription on a template containing 5 Gal4 17mers upstream of a Gal1-LacZ gene fusion (pRJR227). We found that the alanine does participate in transcriptional activation (Table 3).

TABLE 3

Role of $D^{100}$ in Activation by Gal4 (1–100)-Peptide Activators

| Activator | β-galactosidase Activity in JPYP:RJR227 |
|---|---|
| Gal4 | 2958 |
| Gal4(1–100) | 3 |
| LS201 | 5288 |
| LS201ΔD$^{100}$ | 207 |

TABLE 3-continued

Role of $D^{100}$ in Activation by Gal4 (1–100)-Peptide Activators

| Activator | β-galactosidase Activity in JPYP:RJR227 |
|---|---|
| LS164 | 1716 |
| LS164ΔD$^{100}$ | 84 |

Example 2

Analysis of DNA Binding Domain Residues that Contribute to Transcriptional Activation; Identification of Additional Novel Transcriptional Activators Materials and Methods ANALYSIS OF CONTRIBUTING DNA BINDING RESIDUES: Activator LS201, described above in Example 1, was mutagenized according to standard techniques to delete or substitute one or more of Gal4 DNA binding residues 96–100. Transcriptional activation by the resulting proteins was assayed on the pRJR227, as described above.

LINKAGE OF ACTIVATOR PEPTIDE TO PHO4 DNA BINDING DOMAIN: An activating peptide consisting of activator LS201 and Gal4 DNA binding domain residues 96–100 was cloned onto the Pho4 DNA binding domain (residues 153–312, corresponding to Pho4Δ2) by PCR. The resulting construct was introduced into yeast cells and its activating capability was determined by assaying acid phosphatase activity in those cells, and comparing it to cells into which either full-length Pho4 or Pho4Δ2 was introduced. All methods were as described in Gaudreau et al., Cell 89:55, 1997 and Svaren et al., EMBO J. 13:4856, 1994).

Results

Figure 2:
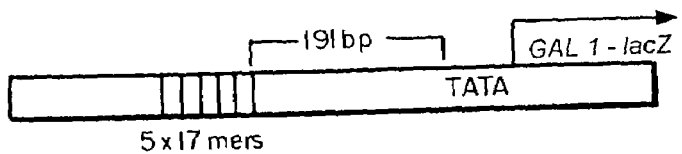
FIG. 2 presents the results of β-galactosidase assays demonstrating how the inventive peptide activator, SEQ ID NO: 167, effects activity levels of mutagenized Gal4-DNA binding domain residues. The unmutagenized Gal4 DNA binding domain is represented by SEQ ID NO: 228.

Gal4 DNA binding domain residues 96–100 were mutagenized in the context of a transcriptional activator comprising peptide LS201, and activation potential of the mutants was assayed on a template in which five consensus Gal4 17mers were positioned upstream of a GAL1-LacZ reporter gene. Gene expression was detected by analysis of β-galactosidase activity. The results are presented in FIG. 2. As can bee seen, deletion of any one of Gal4 residues 96–100 reduced activation 10–2000 fold; substitution of either Phe97 or Val98 with Ala also significantly decreased activation. By contrast, substitution of either Glu99 or Asp100 with Ala had little or no effect on activation. Production of each of the mutant protein was confirmed by gel shift from whole cell extracts (data not shown).

To analyze the role of DNA binding residues further, we asked whether a peptide consisting of activator LS201 and Gal4 residues 96–100 could activate transcription when linked to a different DNA binding domain. Specifically, we linked this peptide to the Pho4 DNA binding domain. We assayed the transcriptional activation capability of our new fusion protein by detecting its ability to stimulate expression of the PHO5 gene, which encodes an acid phosphatase whose enzymatic activity can be analyzed according to known techniques (see Svaren et al., EMBO J. 13:4856, 1994). As shown in FIG. 3, we found that the hybrid activator stimulated transcription as effectively as did full-length Pho4. We note that the fold activation shown in FIG. 3 is misleadingly low due to unrelated acid phosphatase activity in yeast cells that contributes to a high background (e.g., that results in 30 units of activity when no functional activator is probided; see line re Pho4Δ2).

Example 3

In Vitro Activation by Inventive Transcriptional Activators

IN VITRO TRANSCRIPTION WITH YEAST NUCLEAR EXTRACT: In vitro transcription with a yeast nuclear extract was performed as described by Wu et al., EMBO J. 3951, 1996. Specifically, yeast nuclear extract was prepared as described (Ponticelli et al., Mol. Cell. Biol. 10:2832, 1990; Ohashi et al., Mol. Cell. Biol. 14:2731, 1994). Transcription reactions (25 μl) contained 10 mM HEPES, pH 7.5, 10 mM MgSO$_4$, 5 mM EDTA, 10% glycerol, 2.5 mM dithiothreitol, 100 mM potassium glutamate, 10 mM magnesium acetate, 2% polyvinyl alcohol, 8 mM phosphoenolpyruvate, 0.62 nM pG$_2$E4, 5.5 nM pGEM3Z (Promega), and 3 μl yeast nuclear extract, (60 mg/ml). Reactions were incubated with Gal4 protein form 10 min at 25° C. Nucleoside triphosphates were then added to a final concentration of 1 mM and the reactions were allowed to proceed for an additional 60 min at 25° C. Primer extension was performed using an oligonucleotide to the E4 coding sequence as described (Lillie et al., Cell, 46:1043, 1986; Lin et al., Cell, 5:659, 1988).

IN VITRO TRANSCRIPTION WITH YEAST HOLOENZYME: Yeast holoenzyme was prepared as described in Koleske et al., Nature 368:466, 1994 and depicted in FIG. 4. Recombinant TBP and TFIIE were added to the holoenzyme fraction to reconstitute transcriptional activity. Otherwise, reactions were as described above for yeast nuclear extract transcription.

Results

Activator LS201, fused to the Gal4 DNA binding domain, was assayed for its ability to activate transcription. FIG. 5 shows transcriptional activation by the Gal4-LS201 protein on a template containing five consensus Gal4 17mers. The activator stimulated transcription when added in 1, 5, and 30 ng amounts; above those levels (100 ng), the activator squelched transcription. Similar results were obtained when the transcription was mediated by the yeast holoenzyme rather than a nuclear extract (see FIG. 6). In these reactions, Gal4-LS201 activated transcription to levels comparable to those observed with Gal4-VP16. Squelching was again observed at high concentrations of Gal4-LS201.

Example 4

Identification of Novel Transcriptional Activators in Mammalian System

Generally

We will by DNA synthesis extend a gene encoding the DNA binding domain of GAL4 (residues 1–100). The nucleotides will be added without regard to sequence at first, although as results indicate we may bias these sequences (see below). DNA molecules encoding the DNA binding domain fused to additional peptide sequences, attached to a strong promoter, will be transfected into mammalian cells bearing a fluorescent reporter. For example, a fusion gene encoding green fluorescent protein will be put under control of the minimal E1b promoter bearing upstream GAL4 binding sites. Such a reporter will be expressed when bound by an activator. A fluorescence activated cell sorting (FACS) machine will be used to isolate cells expressing the reporter at high levels. We will use PCR to recover the sequence of the new activators. We predict that at least some of these new activators will work at very high efficiencies and yet will have no inhibitory effects on cells even when expressed at high concentrations (see below). We might then take our best activators and subject them to further rounds of peptide addition and screening to find even better activators. We describe the experiment in more details next.

Construction of Stable Reporter Cell Lines

We will use a vector encoding enhanced GFP (EGFP)-neomycin fusion protein as a reporter. EGFP fluoresces 35-fold more intensely and is also more soluble than wild type GFP. Expression of EGFP will allow us to use a FACS machine to separate out cells interest of, whereas the neomycin resistance gene will allow us to obtain our targets as stable cell lines. this double reporter can help us eliminate false positive clones while screening the random library.

The reporter plasmid will be constructed by PCR and restriction enzyme digestion-ligation. Starting from an expression vector, pEGFP-C1 (available from CLONTECH) which contains a selective marker, hygromycin resistance gene, we will fuse a neomycin resistant gene in frame to the C-terminus of EGFP. The DNA cassette, containing five 17 mers of GAL4 high affinity binding sites upstream of the minimal adenovirus E1bTATA promoter, will replace the CMV promoter. The resulting reporter plasmid, pG5EFO, will be transfected into a mammalian cell line (e.g. HeLa, CHO), and hygromycin resistant cells will be selected and cloned to generate the stable reporter cell lines. The reporter cells can be tested by PCR for plasmid integration and by transfection of the activator GAL4-VP16 plasmid for the reporter expression. The reporter cell lines will be maintained in hygromycin medium and should have no or little expression of EGFP and neomycin in the absence of activators.

Construction of Random Libraries

We will start by adding 8 random residues to GAL4 (1–100) DNA binding domain. We will, if needed, extend the random peptide to isolate more potent activators (see below). An oligonucleotide will be synthesized to contain the following: a restriction site, a stop codon (TGA), 24 random nucleotides, and 18 bases which match the 3' end of GAL4 (1–100). The DNA fragment encoding GAL4 (1–100)+X8 will then be generated by PCR using this oligonucleotide and the 5' sequence of GAL4 as primers, and GAL4(1–100) DNA as a template. This PCR fragment will be purified by agarose gel purification, digested with the appropriate restriction enzymes, and ligated into the multiple cloning sites of the plasmid pcDNA3.1/Zeo (from Invitrogen), a high level mammalian expression vector containing Zeocin resistance gene as a selective marker. This ligation reaction will be transformed into the E. coli strain DH5α to generate a library of colonies containing eight random amino acids fused to GAL4(1–100). These colonies will be combined into many pools (~100), in case we use transient transfection to screen the activators (see below). The plasmids will be isolated from these pools, combined, and used to transfect the reporter cells. Theoretically, the library has to contain at least $20^8=2.6\times10^{10}$ primary colonies to cover all the possible sequences. This would be difficult to generate. Our results of yeast activating peptides, however, indicate that activating sequences occur much more frequently. Therefore, we should be able to find activators be screening $10^5$ primary colonies. In addition, our results also suggest that residues in human activating peptides may be similar to that of yeast. We can construct a biased library: we will fuse eight residues of F, L, P, D, and T, as these are the most common in our yeast activating peptides, in random order to GAL4(1–100). We will then only need $5^8=3.9\times10^5$ to cover all the possibilities in this library.

Transfection and Activator Screening

We will transfect the plasmids isolated from the random library into the EGFP-neo reporter cells using the standard methods, such as lipofectAMINE (from Gibco BRL) or calcium phosphate. About 40 hours after transfection, the cells will be trypsinized and flowed through a FAC sorting machine. The cells expressing EGFP at high level can be isolated, and these cells will be replated in the medium supplemented with geneticin (G418) and Zeocin for selection of both activating plasmid and reporter expression. We will maintain these cells in the same medium until individual clones form. These clones will be selected and passed as stable cell lines. In these experiments a GAL4(1–100) expression plasmid will be used as negative control, and GAL4(1–100)+VP16(411–455) (pGAL-VP) as a positive control The activating peptides will be amplified by PCR and recloned into the vector pcDNA3.1/Zeo. the resulting plasmid will be retransfected back into reporter cells to check plasmid linkage. The real activating peptides will be sequenced and the stronger activators will be selected to test their effect on classical activators in squelching assay.

Alternatively, we will try to use transient transfections to screen the mammalian activating peptides. Transient assays do not rely on the integrating efficiency of the plasmid library. Hence, it may be relatively easy for us to obtain the activating peptides. We will transfect the plasmids from different pools of the library and assay the EGFP reporter by FAC scan or by fluorescence microscopy. The activating plasmid pool will be retransformed into E. coli, and the colonies will be pooled at smaller size. The plasmids from the subpools will be transfected into the reporter cells. This process will be repeated until we find a single colony of activating plasmid.

Squelching Assay

We will use transient transfection to test effects of the activators isolated on classic activator VP16. We will cotransfect pGAL-VP and a reporter plasmid with or without the activating peptide plasmid into HELa cells. Here, we will use pG5ELuc containing a luciferase gene instead of EGFP-neomycin as a reporter plasmid because it is readily quantitated. We will harvest transfected cells ~40 hours after transfection and measure luciferase activity using a luminometer machine. We will also include pCMV-lacZ plasmid in our transient transfection assay. pCMV-laxZ encodes a constitutively expressed β-galactosidase which will be assayed and used as an internal control to normalize transfection efficiencies. This assay will allow us to determine if the peptide activators squelch VP16.

After screening these libraries, we expect to find some strong activators that activate transcription by a mechanism different from that of classical activators. We will, if necessary, randomly mutagenize the identified activator(s) at one or two positions(s), or add a few more random residues, and screen for better activators. One advantage of using the FACS sorting is that we can set a threshold to separate the cells expressing EGFP at a level higher than that of the activator we mutagenized. This may allow us to obtain even stronger activators. Such activators will be further characterized and used in studies of sequence specific gene activation.

Example 5

Three-Component Transcriptional Activation System for Identifying Protein—Protein Interactions

Materials and Methods

SYSTEM AND CONSTRUCT: Interaction assay of the three-component transcriptional activation system is performed in yeast strain YW9603, which is derived from yeast strain YT6 (Himmelfarb et al., Cell 63:1699, 1990) by replacing GAL11 gene with a GAL11P allele (N342V) (Barberis et al., Cell 81.359, 1995), and integrating a reporter gene JPY169. The reporter JP169 bears two LexA binding sites 191 base pairs upstream of GAL1 TATA box, followed by LacZ gene. TBP-LexA fusion is expressed from the yeast ACT1 promoter. GAL4 derivatives were described in Wu et al., *EMBO J.*, 1996 (in press), specifically, a GAL4(1–100)+(840–881) fusion gene, and derivatives deleted from the 3' end, were constructed using the polymerase chain reaction (oligonucleotide sequences available on request). These proteins were expressed in yeast from low copy number ARS1/CEN4 plasmids from a fragment of the yeast actin promoter (666 bp 5' to the ATG of ACT1). All regions of plasmids that had been subjected to PCR were sequenced to ensure that the correct fusion construct had been made, and that no mutations had arisen during amplification.

SURFACE PLASMON RESONANCE SENSORCHIP PREPARATION: In vitro affinities are measured by Surface Plasmon Resonance, as described in Wu et al., *EMBO J.*, 1996 (in press). Specifically, the dextran surface of Sensorchip CM5 was activated by two consecutive 40 µl injections of NHS/EDC (Pharmacia) at a flow rate of 2 µl per minute. Streptavidin (Sigma) was then coupled to the activated dextran by injecting 10 µl of 0.1 mg/ml solution in 10 mM NaOAc, pH 4.5 at a flow rate of 2 µl per minute. The excess of activated dextran was blocked by two consecutive 40 µl injections ethanolamine at a flow rate of 2 µl per minute. This procedure prolonged the activation and blocking time (from the usual 7 minutes to 40 minutes) so that the negative charges on the dextran surface was greatly reduced. A 50mer DNA oligo (sequence available upon request) carrying two consensus GAL4 binding sites was synthesized with a biotin group attached to the 5' end. It was annealed to its complementary oligo (without biotin) by heating to 75° C. followed by slow cooling. The resulting double strand DNA carries two GAL4 binding sites and is biotinylated at one end. 10 µl of the biotinylated DNA (6.25 µg/ml) was injected to the streptavidin immobilized chip at a flow rate of 5 µl per minute. The average result of the procedure is that ~3000 RU's of streptavidin was immobilized and ~600 RU's of DNA was attached to the chip. After the first regeneration (by washing with 10 µl 0.1% SDS), the DNA bearing sensorchip becomes very stable and it could sustain many rounds of regeneration without significant changes in the baseline levels. This DNA bearing chip was used to capture GAL4 derivatives in such a conformation that the activating regions were uniformly presented and their interactions with other proteins were studied. In control experiments, GAL80, TBP and TFIIB did not bind detectably to the DNA bearing chip (data not shown). The amine coupling method published in the BIAcore manual (Pharmacia Biosensor AB, 1994) differs from ours as follows: the activation of dextran surface by NHS/EDC, binding of ligand, and blocking of excess activated dextran by ethanolamine was each performed by a single injecting of 35 µl volume at a flow rate of 5 µl/min. This method produced chips that, in our preliminary experiments, bound TBP and TFIIB significantly, probably because of the relatively large amount of negative charge remaining on the unactivated portion of the sensorchip.

PROTEIN—PROTEIN INTERACTIONS: The activators (GAL4 derivatives and other activating regions fused to GAL4 DNA binding domain) were first passed over the DNA-bearing chip. Typically 10 µl of 0.01 mg/ml protein solution (~1 µM) in HBS (10 mM HEPES pH 7.4, 150 mM NaCl, 0.0005% Surfectant P20, Pharmacia) were injected at a flow rate of 5 µl/min, and the DNA was saturated by the activators. This is indicated by the first increase of the RU value on the sensorgrams. Various proteins to be tested (e.g., TBP) were then injected (typically 20 µl of 1 mM solution in HBS at a flow rate of 5 µl/min), and their binding to the activating regions was indicated by the second increase of the RU value on the sensogram. The DNA bearing chip was then regenerated by washing with 10 µl of 0.1% SDS, a procedure that washes both proteins off the DNA, but leaves the DNA bearing chip intact. The baseline of the sensorgrams always comes back to the original level after each regeneration. A different activator was then injected to the same surface at the same concentration, and the DNA was once again saturated with the activators. As a consequence the same number of the molecules of the activators was immobilized to the chip each time. The protein to be tested (e.g., TBP) was once again injected and its binding to this activator was compared to that of the previous one. This comparison, we believe, is highly accurate because the exact same concentration of the same protein to be tested (e.g., TBP) was injected, and same number of molecules of activators was immobilized each time. GAL4 DNA binding domain alone was used as a negative control for each tested protein.

KINETIC EVALUATION: The apparent kinetic constants ($k_{on}$ and $k_{off}$) of TBP, TFIIB and other tested proteins binding to various activators were the protein to be tested (e.g., TBP) was injected, followed by an injection of 10 µl 0.1% SDS to regenerate the sensorchip. The activator was injected at the same concentration in each sensorgram, but the protein to be tested (e.g., TBP) was injected 7 different concentrations in 2 fold serial increases (e.g., TBP was injected at 0.0625 µM, 0.125 µM, 0.25 µM, 0.5 µM, 1 µM, 2 µM and 4 µM). All of the injections were performed at a flow rate of 5 µl/min. A sensorgram of a blank buffer injection following the injection of the activator was subtracted from each of the 7 sensorgrams showing different concentrations of the tested proteins (e.g. TBP) binding to the activator. The resulting sensorgrams corrected for the slow decay of the activators from the DNA. This correction in fact did not significantly change the calculated $K_D$'S. The binding kinetics of all the interactions fit well to the first order kinetics model, and the $k_{on}$ and $k_{off}$ was solved using linear regression algorithm. The apparent equilibrium constant $K_D$ was obtained by dividing $k_{off}$ with $k_{on}$.

Results

We employed TBP and Gal4 region II' (G4RII'), as interaction partners in a three-component screen. Specifically, we fused TBP to the LexA DNA binding domain and fused G4RII' (as Gal4(840–881)) to Gal4(1–100). We introduced these constructs into Gal11 and Gal11P yeast cells bearing a reporter that included two LexA binding sites upstream of a GAL1-LacZ reporter construct. We compared the expression levels of the LacZ gene in Gal11 and Gal11P cells by plate assay. Our results are presented in Table 4.

TABLE 4

G4RII'-TBP Interaction Assayed in Three-Component Transcriptional Activation System

| Gal4 Derivative | In vitro Affinity for TBP | Blueness on X-Gal plates |
| --- | --- | --- |
| (1–100) + (840–881) | $6 \times 10^6 \, M^{-1}$ | +++ |
| (1–100) + (840–857) | $2 \times 10^6 \, M^{-1}$ | + |
| (1–100) + nothing | $0 \times 10^6 \, M^{-1}$ | − |

Example 6

Production and Characterization of TBP Mutants that Enhance Transcriptional Activation The TBP mutations N69R and V71R were isolated from screening a TBP mutant library in yeast strain YW9510, derived from JPY9 by integrating reporter gene RY131 and expressing a GAL4 derivative GAL4(1–100)+(858–881)F869A (Wu et al, *EMBO J.*, 1996, in press). TBP-encoding plasmids in darker blue colonies on X-gal plates were rescued and characterized, yielding the above mutations. β-galactosidase activity was measured in YW9510 carrying these mutant TBP's and wild type TBP's.

The results are presented below in Table 5:

TABLE 5

Transcriptional Activation by Gal4(1–100; 858–881)F869A in the Presence of TBP Mutants

| TBP derivative | β-galactosidase units |
| --- | --- |
| Wild-type | 53 |
| V71R | 121 |
| N69R | 125 |

These mutations were tested in a yeast strain expressing a LexA-GAL11 fusion protein and a reporter gene carrying two LexA sites 1,200 base pairs away from the GAL1-LacZ TATA box. The results are shown below in Table 6:

TABLE 6

Transcriptional Activation by LexA-Gal11 in the Presence of TBP Mutants

| TBP derivative | β-galactosidase units |
| --- | --- |
| Wild-type | 13 |
| V71R | 164 |
| N69R | 192 |

---

The invention claimed is:

1. A transcriptional activator comprising:

a DNA binding moiety; and a transcription activation peptide that is at least approximately 25% hydrophobic and wherein the peptide is 6, 8, 11, or 13 amino acids in length, which peptide is linked to the DNA binding moiety in a manner that does not interfere with its DNA binding activity, the transcription activation peptide being both necessary and sufficient to activate transcription, the transcriptional activator being characterized by an ability, when expressed in yeast cells, to activate transcription from a promoter including a recognition site for the DNA binding moiety approximately 250–1000 basepairs upstream of the transcription start site, the transcriptional activator being characterized by an inability to squelch transcriptional activation by LexA-Gal4 when expressed in yeast.

2. A transcriptional activator comprising:
a DNA binding moiety; and
a transcription activation peptide that is at least approximately 25% hydrophobic and is between about 6 and 25 amino acids in length, which peptide is linked to the DNA binding moiety comprising Gal4(1–100) in a manner that does not interfere with its DNA binding activity, the transcription activation peptide being both necessary and sufficient to activate transcription,
the transcriptional activator being characterized by an ability, when expressed in yeast cells, to activate transcription from a promoter including a recognition site for the DNA binding moiety at least half as well as does Gal4 from a promoter containing at least one Gal4 DNA binding site approximately 250–1000 basepairs upstream of the transcription start site,
the transcriptional activator being characterized by an inability to squelch transcriptional activation by LexA-Gal4 when expressed in yeast.

3. A transcriptional activator comprising:
a DNA binding moiety; and
a transcription activation peptide that is selected from the group consisting of LS4 (QLPPWL; SEQ ID NO: 8); LS8 (QFLDAL; SEQ ID NO: 16); LS11 (LDSFYV; SEQ ID NO: 21); LS12 (PPPPWP; SEQ ID NO: 23); LS17 (SWFDVE; SEQ ID NO: 33); LS19 (QLPDLF; SEQ ID NO: 37); LS20 (PLPDLF; SEQ ID NO: 39); LS21 (FESDDI; SEQ ID NO: 41); LS24 (QYDLFP; SEQ ID NO: 45); LS25 (LPDLIL; SEQ ID NO: 47); LS30 (LPDFDP; SEQ ID NO: 55); LS35 (LFPYSL; SEQ ID NO: 57); LS51 (FDPFNQ; SEQ ID NO: 71); LS64 (DFDVLL; SEQ ID NO: 85); LS102 (HPPPPI; SEQ ID NO: 92); LS105 (LPGCFF; SEQ ID NO: 95); LS106 (QYDLFD; SEQ ID NO: 97); LS120 (YPPPPF; SEQ ID NO: 115); LS123 (PLPPFL; SEQ ID NO: 118); LS135 (LPPPWL; SEQ ID NO: 136); LS136 (VWPPAV; SEQ ID NO: 138); LS152 (DPPWYL; SEQ ID NO: 154); LS153 (LY; SEQ ID NO: 156); LS158 (FDPFGL; SEQ ID NO: 160); LS160 (PPSVNL; SEQ ID NO: 162); LS201 (YLLPTCIP; SEQ ID NO: 167); LS202 (LQVHNST; SEQ ID NO: 169); LS203 (VLDFTPFL; SEQ ID NO: 171); LS206 (HHAFYEIP; SEQ ID NO: 175); LS212 (PWYPTPYL; SEQ ID NO: 183); LS223 (YLLPFLPY; SEQ ID NO: 195); LS225 (YFLPLLST; SEQ ID NO: 199); LS232 (FSPTFWAF; SEQ ID NO: 209); LS241 (LIMNWPTY; SEQ ID NO: 221), each of these peptides extended at its amino terminal end by Gal4 residues 96–100, and each of these peptides extended at its amino terminal end by Gal4 96–100 except that one or both of Gal4 residues 99 and 100 has been substituted with a different amino acid;
which peptide is linked to the DNA binding moiety in a manner that does not interfere with its DNA binding activity, the transcription activation peptide being both necessary and sufficient to activate transcription,
the transcriptional activator being characterized by an ability, when expressed in yeast cells, to activate transcription from a promoter including a recognition site for the DNA binding moiety approximately 250–1000 basepairs upstream of the transcription start site,
the transcriptional activator being characterized by an inability to squelch transcriptional activation by LexA-Gal4 when expressed in yeast.

\* \* \* \* \*

SEQUENCE LISTING

```
<160> NUMBER OF SEQ ID NOS: 238

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 1

Trp Thr Asp Gln Thr Ala Tyr Asn Ala Phe Gly
 1               5                  10

<210> SEQ ID NO 2
<211> LENGTH: 18
<212> TYPE: DNA
<213> ORGANISM: Artificial Sequence
<220> FEATURE:
<221> NAME/KEY: misc_feature
<222> LOCATION: (9)..(10)
<223> OTHER INFORMATION: n = a single nucleotide.
<220> FEATURE:
<221> NAME/KEY: misc_feature
<222> LOCATION: (12)..(13)
<223> OTHER INFORMATION: n = a single nucleotide.
<220> FEATURE:
<223> OTHER INFORMATION: Description of Artificial Sequence: Random
      nucleotide sequences.

<400> SEQUENCE: 2
ccnctcttnn cnncnctc                                                  18

<210> SEQ ID NO 3
<211> LENGTH: 18
<212> TYPE: DNA
```

```
<213> ORGANISM: Artificial Sequence
<220> FEATURE:
<223> OTHER INFORMATION: Description of Artificial Sequence: Random
      nucleotide sequences.

<400> SEQUENCE: 3
attccgccac cgtatttc                                               18

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 4

Ile Pro Pro Pro Tyr Phe
 1               5

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 5
ctgcccgggt ctttcttc                                               18

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 6

Leu Pro Gly Cys Phe Phe
 1               5

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 7
cagctccccc cctggtta                                               18

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 8

Gln Leu Pro Pro Trp Leu
 1               5

<210> SEQ ID NO 9
```

```
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 9
tactggccct ccccttc                                              18

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 10

Tyr Trp Pro Ser Pro Phe
  1               5

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 11
gagttcccct atgacttg                                             18

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence:Random
      nucleotide sequences.

<400> SEQUENCE: 12

Glu Phe Pro Tyr Asp Leu
  1               5

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:Random
      peptide sequences.

<400> SEQUENCE: 13
accgccgaat tccccctc                                             18

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 14

Thr Ala Glu Phe Pro Leu
  1               5
```

```
<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 15
caatttctag acgcactt                                                       18

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 16

Gln Phe Leu Asp Ala Leu
 1               5

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 17
acattccctg accccttc                                                       18

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 18

Thr Phe Pro Asp Pro Phe
 1               5

<210> SEQ ID NO 19
<211> LENGTH: 18
<212> TYPE: DNA
<213> ORGANISM: Artificial Sequence
<220> FEATURE:
<221> NAME/KEY: misc_feature
<222> LOCATION: (10)
<223> OTHER INFORMATION: n = a single nucleotide.
<220> FEATURE:
<221> NAME/KEY: misc_feature
<222> LOCATION: (12)
<223> OTHER INFORMATION: n = a single nucleotide.
<220> FEATURE:
<223> OTHER INFORMATION: Description of Artificial Sequence:Random
      nucleotide sequences.

<400> SEQUENCE: 19
atcggcccan cnctttc                                                        18

<210> SEQ ID NO 20
<211> LENGTH: 18
<212> TYPE: DNA
```

```
<213> ORGANISM: Artificial Sequence
<220> FEATURE:
<223> OTHER INFORMATION: Description of Artificial Sequence:Random
      nucleotide sequences.

<400> SEQUENCE: 20
ttggattttt cctacgtc                                                    18

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 21

Leu Asp Phe Ser Tyr Val
 1               5

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 22
cccccaccac cctggccc                                                    18

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 23

Pro Pro Pro Pro Trp Pro
 1               5

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 24
ctctttgaat gaggaacc                                                    18

<210> SEQ ID NO 25
<211> LENGTH: 3
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 25

Leu Phe Glu
 1

<210> SEQ ID NO 26
```

```
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 26
ctgctcgaca tacctttc                                                        18

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 27

Leu Leu Asp Thr Phe
 1               5

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 28
ctccccgacg cctttctc                                                        18

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 29

Leu Pro Asp Ala Phe Leu
 1               5

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 30
ctcttccccg acctcaac                                                        18

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 31

Leu Phe Pro Asp Leu Asn
 1               5
```

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 32
tcttggtttg atgtcgaa                                              18

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 33

Ser Trp Phe Asp Val Glu
 1               5

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 34
cttgaacctc cgccctgg                                              18

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 35

Leu Glu Pro Pro Pro Trp
 1               5

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 36
cagctacctg atctgttc                                              18

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 37

Gln Leu Pro Asp Leu Phe

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence:Random nucleotide sequences.

<400> SEQUENCE: 38
cctctcccag acctcttc                                                18

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence:Random peptide sequences.

<400> SEQUENCE: 39

Pro Leu Pro Asp Leu Phe
 1               5

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence:Random nucleotide sequences.

<400> SEQUENCE: 40
ttcgaattcg atgatatc                                                18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence:Random nucleotide sequences.

<400> SEQUENCE: 41 accttttcg ataccccc                                                 18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence:Random nucleotide sequences.

<400> SEQUENCE: 42 accttttcg ataccccc                                                 18

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence:Random peptide sequences.

<400> SEQUENCE: 43

Thr Phe Phe Asp Thr Pro
1               5

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 44
caatacgatc tattcgat                                           18

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 45

Gln Tyr Asp Leu Phe Asp
1               5

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 46
ctaccggact taattctc                                           18

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 47

Leu Pro Asp Leu Ile Leu
1               5

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence:Random
      peptide sequences.

<400> SEQUENCE: 48 cccccctgg atccatgg                                            18

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

```
<400> SEQUENCE: 49

Pro Pro Leu Asp Pro Trp
 1               5

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 50
caatacgatc tattcgat                                                  18

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 51

Gln Tyr Asp Leu Phe Asp
 1               5

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 52
accttgtgac gcgacagc                                                  18

<210> SEQ ID NO 53
<211> LENGTH: 2
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 53

Thr Leu
 1

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 54
ctaccagact tcgatcca                                                  18

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence:Random
``` peptide sequences.

<400> SEQUENCE: 55

Leu Pro Asp Phe Asp Pro
 1               5

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 56
ctaatcccat actccctg                                                  18

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 57

Leu Phe Pro Tyr Ser Leu
 1               5

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 58
tttcctgacc tcttcccc                                                  18

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 59

Phe Pro Asp Leu Phe Pro
 1               5

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 60
cctaacccct tcccactg                                                  18

<210> SEQ ID NO 61
<211> LENGTH: 6
<212> TYPE: PRT
<213> ORGANISM: Artificial Sequence

```
<220> FEATURE:
<223> OTHER INFORMATION: Description of Artificial Sequence:Random
      peptide sequences.

<400> SEQUENCE: 61

Pro Asn Pro Phe Pro Leu
 1               5

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 62
ttctagaaca cacccccg                                               18

<210> SEQ ID NO 63
<211> LENGTH: 1
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 63

Phe
 1

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 64
cccccccccc aatatttc                                               18

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 65

Pro Pro Pro Gln Tyr Phe
 1               5

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 66
gaggacaccc cccctgg                                                18

<210> SEQ ID NO 67
<211> LENGTH: 6
```

```
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 67

Glu Asp Thr Pro Pro Trp
  1               5

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 68
ttcccccccc ccccattc                                                 18

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 69

Phe Pro Pro Pro Pro Phe
  1               5

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 70 ttcccccat tcaaccaa                                                  18

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 71

Phe Pro Pro Phe Asn Gln
  1               5

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 72 ccoctgttct gacacgga                                                 18
```

```
<210> SEQ ID NO 73
<211> LENGTH: 3
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 73

Pro Leu Phe
  1

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 74
accggtccac cagagcta                                                   18

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 75

Thr Gly Pro Pro Glu Leu
  1               5

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence:Random
      nucleotide  sequences.

<400> SEQUENCE: 76
ctaatcccat actccctg                                                   18

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 77

Leu Ile Pro Tyr Ser Leu
  1               5

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 78
accttccctt actcactg                                                   18
```

```
<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence:Random
      nucleotide sequences.

<400> SEQUENCE: 79

Thr Phe Pro Tyr Ser Leu
 1               5

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence:Random
      peptide sequences.

<400> SEQUENCE: 80
ggcagcttcg aactcctc                                                18

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 81

Gly Ser Phe Glu Leu Leu
 1               5

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 82
ctggaatacc ccaccacc                                                18

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 83

Leu Glu Tyr Pro Thr Thr
 1               5

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 84
```
aattttgatg acctactc                                    18

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 85

Asn Phe Asp Asp Leu Leu
 1               5

<210> SEQ ID NO 86
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 86
ctggacgtat tttcacac                                    18

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 87

Leu Asp Val Phe Ser His
 1               5

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 88
cagctacctg atctgttc                                    18

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 89

Gln Leu Pro Asp Leu Phe
 1               5

<210> SEQ ID NO 90
<211> LENGTH: 19
<212> TYPE: DNA
<213> ORGANISM: Artificial Sequence
<220> FEATURE:
<223> OTHER INFORMATION: Description of Artificial Sequence:Random
      nucleotide sequences.

```
<400> SEQUENCE: 90
cacccccccc cctcccatt                                                   19

<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 91

His Pro Pro Pro Pro Ile
  1               5

<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 92
cccctgttct gactcgga                                                    18

<210> SEQ ID NO 93
<211> LENGTH: 3
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 93

Pro Leu Phe
  1

<210> SEQ ID NO 94
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 94
ctgcccgggt gtttcttc                                                    18

<210> SEQ ID NO 95
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 95

Leu Pro Gly Cys Phe Phe
  1               5

<210> SEQ ID NO 96
<211> LENGTH: 18
<212> TYPE: DNA
<213> ORGANISM: Artificial Sequence
<220> FEATURE:
```

```
<223> OTHER INFORMATION: Description of Artificial Sequence:Random
      nucleotide sequences.

<400> SEQUENCE: 96
caatacgatc tattcgat                                                       18

<210> SEQ ID NO 97
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 97

Gln Tyr Asp Leu Phe Asp
 1               5

<210> SEQ ID NO 98
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 98
gctctcccgc cgtacctc                                                       18

<210> SEQ ID NO 99
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 99

Ala Leu Pro Pro Tyr Leu
 1               5

<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 100
ttcctcccct cccttccc                                                       18

<210> SEQ ID NO 101
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 101

Phe Leu Pro Ser Leu Pro
 1               5

<210> SEQ ID NO 102
<211> LENGTH: 18
<212> TYPE: DNA
```

```
<213> ORGANISM: Artificial Sequence
<220> FEATURE:
<223> OTHER INFORMATION: Description of Artificial Sequence:Random
      nucleotide sequences.

<400> SEQUENCE: 102
atccctctcc tctgtctc                                                    18

<210> SEQ ID NO 103
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 103

Ile Pro Leu Leu Cys Leu
 1               5

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 104
atgctccctc cctacatc                                                    18

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 105

Met Leu Pro Pro Tyr Ile
 1               5

<210> SEQ ID NO 106
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 106
cccccctaca tatggcca                                                    18

<210> SEQ ID NO 107
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 107

Pro Pro Tyr Ile Trp Pro
 1               5

<210> SEQ ID NO 108
```

```
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 108
gcgctatggt agctaccc                                              18

<210> SEQ ID NO 109
<211> LENGTH: 3
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 109

Ala Leu Trp
  1

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 110
gacctcaata ttttctag                                              18

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 111

Asp Leu Asn Ile Phe
  1               5

<210> SEQ ID NO 112
<211> LENGTH: 18
<212> TYPE: DNA
<213> ORGANISM: Artificial Sequence
<220> FEATURE:
<221> NAME/KEY: misc_feature
<222> LOCATION: (12)
<223> OTHER INFORMATION: n = a single nucleotide
<220> FEATURE:
<223> OTHER INFORMATION: Description of Artificial Sequence:Random
      nucleotide sequences.

<400> SEQUENCE: 112
ctacccatga cnccgttc                                              18

<210> SEQ ID NO 113
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 113
```

Leu Pro Met Thr Pro Phe
 1               5

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 114 tacccccgc cgcccttt                                                    18

<210> SEQ ID NO 115
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 115

Tyr Pro Pro Pro Pro Phe
 1               5

<210> SEQ ID NO 116
<211> LENGTH: 18
<212> TYPE: DNA
<213> ORGANISM: Artificial Sequence
<220> FEATURE:
<221> NAME/KEY: misc_feature
<222> LOCATION: (1)..(3)
<223> OTHER INFORMATION: n = a single nucleotide
<220> FEATURE:
<221> NAME/KEY: misc_feature
<222> LOCATION: (11)..(12)
<223> OTHER INFORMATION: n = a single nucleotide
<220> FEATURE:
<221> NAME/KEY: misc_feature
<222> LOCATION: (14)
<223> OTHER INFORMATION: n = a single nucleotide
<220> FEATURE:
<223> OTHER INFORMATION: Description of Artificial Sequence:Random
      nucleotide sequences.

<400> SEQUENCE: 116
nnncccgtag nncnctgg                                                   18

<210> SEQ ID NO 117
<211> LENGTH: 18
<212> TYPE: DNA
<213> ORGANISM: Artificial Sequence
<220> FEATURE:
<221> NAME/KEY: misc_feature
<222> LOCATION: (9)
<223> OTHER INFORMATION: n = a single nucleotide
<220> FEATURE:
<223> OTHER INFORMATION: Description of Artificial Sequence:Random
      nucleotide sequences.

<400> SEQUENCE: 117 cccttccnc cttttctt                                                    18

<210> SEQ ID NO 118
<211> LENGTH: 6
<212> TYPE: PRT
<213> ORGANISM: Artificial Sequence
<220> FEATURE:

<223> OTHER INFORMATION: Description of Artificial Sequence:Random
      peptide sequences.

<400> SEQUENCE: 118

Pro Leu Pro Pro Phe Leu
 1               5

<210> SEQ ID NO 119
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 119
ctccccacca tgcccctc                                                18

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 120

Leu Phe Leu Pro Pro Thr
 1               5

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 121
ctcttcctac cacccacc                                                18

<210> SEQ ID NO 122
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 122

Leu Phe Leu Pro Pro Thr
 1               5

<210> SEQ ID NO 123
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 123
accgccgaat tcccctc                                                 18

<210> SEQ ID NO 124
<211> LENGTH: 6
<212> TYPE: PRT

```
<213> ORGANISM: Artificial Sequence
<220> FEATURE:
<223> OTHER INFORMATION: Description of Artificial Sequence:Random
      peptide sequences.

<400> SEQUENCE: 124

Thr Ala Glu Phe Pro Leu
  1               5

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 125
accgatttcc ttctgctg                                                 18

<210> SEQ ID NO 126
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 126

Thr Asp Phe Leu Leu Leu
  1               5

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 127
ggagaatatt tcccttc                                                  18

<210> SEQ ID NO 128
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 128

Gly Glu Tyr Phe Pro Phe
  1               5

<210> SEQ ID NO 129
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 129
tttatagatc ccctctc                                                  18

<210> SEQ ID NO 130
```

-continued

```
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 130

Phe Ile Asp Pro Pro Leu
 1               5

<210> SEQ ID NO 131
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 131
ctaatcccat actccctg                                              18

<210> SEQ ID NO 132
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 132

Leu Ile Pro Tyr Ser Leu
 1               5

<210> SEQ ID NO 133
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 133
caatacgatc tattcgat                                              18

<210> SEQ ID NO 134
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 134

Gln Tyr Asp Leu Phe Asp
 1               5

<210> SEQ ID NO 135
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 135
ttacctcccc cctggctt                                              18
```

```
<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 136

Leu Pro Pro Pro Trp Leu
 1               5

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 137
ctctggccac ctgccgta                                                   18

<210> SEQ ID NO 138
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 138

Val Trp Pro Pro Ala Val
 1               5

<210> SEQ ID NO 139
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 139
ccaacaaact cctactga                                                   18

<210> SEQ ID NO 140
<211> LENGTH: 5
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 140

Pro Thr Asn Phe Tyr
 1               5

<210> SEQ ID NO 141
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 141
```
ctaatcccat acttcctg                                                18

<210> SEQ ID NO 142
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 142

Leu Ile Pro Tyr Phe Leu
 1               5

<210> SEQ ID NO 143
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 143
atctgcgaga gtttctttt                                               18

<210> SEQ ID NO 144
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 144

Ile Cys Glu Ser Phe Phe
 1               5

<210> SEQ ID NO 145
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 145
gcggacccgt ggctactc                                                18

<210> SEQ ID NO 146
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 146

Ala Asp Pro Trp Leu Leu
 1               5

<210> SEQ ID NO 147
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

```
<400> SEQUENCE: 147
gcgcagtacc ctttcttc                                              18

<210> SEQ ID NO 148
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 148

Ala Gln Tyr Pro Phe Phe
 1               5

<210> SEQ ID NO 149
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 149
cctccgtcat tcttcggc                                              18

<210> SEQ ID NO 150
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 150

Pro Pro Ser Phe Phe Gly
 1               5

<210> SEQ ID NO 151
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 151
ctttccagcc ttcccttc                                              18

<210> SEQ ID NO 152
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 152

Pro Ser Ser Leu Pro Phe
 1               5

<210> SEQ ID NO 153
<211> LENGTH: 18
<212> TYPE: DNA
<213> ORGANISM: Artificial Sequence
<220> FEATURE:
<223> OTHER INFORMATION: Description of Artificial Sequence:Random
```

-continued

<210> SEQ ID NO 153

<400> SEQUENCE: 153
gacccaccat ggtacctt                                                    18

<210> SEQ ID NO 154
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 154

Asp Pro Pro Trp Tyr Leu
 1               5

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 155
ctctactaat aataagca                                                    18

<210> SEQ ID NO 156
<211> LENGTH: 2
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 156

Leu Tyr
 1

<210> SEQ ID NO 157
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 157
cctatccccg gtttcact                                                    18

<210> SEQ ID NO 158
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 158

Pro Ile Pro Gly Phe Thr
 1               5

<210> SEQ ID NO 159
<211> LENGTH: 18
<212> TYPE: DNA
<213> ORGANISM: Artificial Sequence

```
<220> FEATURE:
<223> OTHER INFORMATION: Description of Artificial Sequence:Random
      nucleotide sequences.

<400> SEQUENCE: 159
tttgacccct tgggcatc                                              18

<210> SEQ ID NO 160
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 160

Phe Asp Pro Phe Gly Ile
 1               5

<210> SEQ ID NO 161
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 161 cccccccagtg tgaacctc                                             18

<210> SEQ ID NO 162
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 162

Pro Pro Ser Val His Leu
 1               5

<210> SEQ ID NO 163
<211> LENGTH: 18
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 163
ccagacaacg tcctaccg                                              18

<210> SEQ ID NO 164
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 164

Pro Asp Asn Val Leu Pro
 1               5

<210> SEQ ID NO 165
<211> LENGTH: 11
```

```
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 165

Lys Ala Leu Leu Thr Gly Leu Phe Val Gln Asp
  1               5                  10

<210> SEQ ID NO 166
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 166 tacctttta caacctgtat acct                                              24

<210> SEQ ID NO 167
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 167

Tyr Leu Leu Pro Thr Cys Ile Pro
  1               5

<210> SEQ ID NO 168
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 168
ctacaagtcc acaacagcag atag                                             24

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 169

Leu Gln Val His Asn Ser Thr
  1               5

<210> SEQ ID NO 170
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 170
gttcttgact tcacccettt cctc                                             24
```

```
<210> SEQ ID NO 171
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 171

Val Leu Asp Phe Thr Pro Phe Leu
  1               5

<210> SEQ ID NO 172
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 172 cccccttacct acccccctcgc cgga                                         24

<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 173

Pro Leu Thr Tyr Pro Leu Ala Gly
  1               5

<210> SEQ ID NO 174
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 174
ctcctcgcct tttacgagat accg                                           24

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 175

Leu Leu Ala Phe Tyr Glu Ile Pro
  1               5

<210> SEQ ID NO 176
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 176 cccccctgaca cctacatctt ctta                                          24
```

```
<210> SEQ ID NO 177
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 177

Pro Pro Asp Thr Tyr Ile Phe Phe
  1               5

<210> SEQ ID NO 178
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 178
caactcaact acccactcgc cata                                              24

<210> SEQ ID NO 179
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 179

Gln Leu Asn Tyr Pro Leu Ala Ile
  1               5

<210> SEQ ID NO 180
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 180
ctcgtactac cccagccgca actc                                              24

<210> SEQ ID NO 181
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 181

Leu Val Leu Pro Gln Pro Gln Leu
  1               5

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 182
```

```
ccttggtacc ctacgccgta tctg                                          24
```

<210> SEQ ID NO 183
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 183

Pro Trp Tyr Pro Thr Pro Tyr Leu
 1               5

<210> SEQ ID NO 184
<211> LENGTH: 27
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 184

```
tggctccgat cgttcagccc gtatctg                                       27
```

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 185

Trp Leu Arg Ser Phe Ser Val Pro
 1               5

<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 186

```
cttgaaccat cactatatat gata                                          24
```

<210> SEQ ID NO 187
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 187

Leu Glu Pro Ser Leu Tyr Met Ile
 1               5

<210> SEQ ID NO 188
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 188
tgcatcttgt cccaccacgc tcct 24

<210> SEQ ID NO 189
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 189

Cys Ile Leu Ser His His Ala Pro
 1               5

<210> SEQ ID NO 190
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 190
gacctcacat gctgtttttg cctc 24

<210> SEQ ID NO 191
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 191

Asp Leu Thr Cys Cys Phe Cys Leu
 1               5

<210> SEQ ID NO 192
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 192
ccgtttattg gcggcccttta cgca 24

<210> SEQ ID NO 193
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 193

Pro Phe Ile Gly Gly Pro Tyr Ala
 1               5

<210> SEQ ID NO 194
<211> LENGTH: 24
<212> TYPE: DNA
<213> ORGANISM: Artificial Sequence
<220> FEATURE:

```
<223> OTHER INFORMATION: Description of Artificial Sequence:Random
      nucleotide sequences.

<400> SEQUENCE: 194
tacctactac ctttccttcc gtac                                              24

<210> SEQ ID NO 195
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 195

Tyr Leu Leu Pro Phe Leu Pro Tyr
  1               5

<210> SEQ ID NO 196
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 196
tacccctggt ttccagtccc ctta                                              24

<210> SEQ ID NO 197
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 197

Tyr Pro Trp Phe Pro Val Pro Phe
  1               5

<210> SEQ ID NO 198
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 198
tatttactac ctctcctctc cact                                              24

<210> SEQ ID NO 199
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 199

Tyr Phe Leu Pro Leu Leu Ser Thr
  1               5

<210> SEQ ID NO 200
<211> LENGTH: 24
<212> TYPE: DNA
```

```
<213> ORGANISM: Artificial Sequence
<220> FEATURE:
<223> OTHER INFORMATION: Description of Artificial Sequence:Random
      nucleotide sequences.

<400> SEQUENCE: 200
ctctccattc aaccctattt tttt                                              24

<210> SEQ ID NO 201
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 201

Leu Ser Ile Gln Pro Tyr Phe Phe
  1               5

<210> SEQ ID NO 202
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 202
gccctattct acctcctcta aaag                                              24

<210> SEQ ID NO 203
<211> LENGTH: 6
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 203

Ala Leu Phe Tyr Leu Leu
  1               5

<210> SEQ ID NO 204
<211> LENGTH: 24
<212> TYPE: DNA
<213> ORGANISM: Artificial Sequence
<220> FEATURE:
<221> NAME/KEY: misc_feature
<222> LOCATION: (3)
<223> OTHER INFORMATION: n = a single nucleotide
<220> FEATURE:
<221> NAME/KEY: misc_feature
<222> LOCATION: (18)
<223> OTHER INFORMATION: n = a single nucleotide
<220> FEATURE:
<223> OTHER INFORMATION: Description of Artificial Sequence:Random
      nucleotide sequences.

<400> SEQUENCE: 204
ccntggccct actatttncc gatc                                              24

<210> SEQ ID NO 205
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.
```

```
<400> SEQUENCE: 205

Pro Trp Pro Tyr Tyr Phe Pro Ile
  1               5

<210> SEQ ID NO 206
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 206
ccgatttggc aatataccat tttc                                            24

<210> SEQ ID NO 207
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 207

Pro Ile Trp Gln Tyr Thr Ile Phe
  1               5

<210> SEQ ID NO 208
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 208
ttatccccca cctttgggc attc                                             24

<210> SEQ ID NO 209
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 209

Phe Ser Pro Thr Phe Trp Ala Phe
  1               5

<210> SEQ ID NO 210
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 210
gaccccccct acgcctatac tctg                                            24

<210> SEQ ID NO 211
<211> LENGTH: 8
<212> TYPE: PRT
<213> ORGANISM: Artificial Sequence
<220> FEATURE:
```

```
<223> OTHER INFORMATION: Description of Artificial Sequence:Random
      peptide sequences.

<400> SEQUENCE: 211

Phe Pro Pro Tyr Ala Tyr Thr Leu
  1               5

<210> SEQ ID NO 212
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 212
cctgcactcc tgtttccatt catc                                          24

<210> SEQ ID NO 213
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 213

Pro Ala Leu Leu Phe Pro Phe Ile
  1               5

<210> SEQ ID NO 214
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 214
ttcacctacg ctctcccctt cccc                                          24

<210> SEQ ID NO 215
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 215

Phe Thr Tyr Ala Leu Pro Phe Pro
  1               5

<210> SEQ ID NO 216
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 216
ctcttaccac tgcctctctt cctc                                          24

<210> SEQ ID NO 217
<211> LENGTH: 8
<212> TYPE: PRT
```

<213> ORGANISM: Artificial Sequence
<220> FEATURE:
<223> OTHER INFORMATION: Description of Artificial Sequence:Random
      peptide sequences.

<400> SEQUENCE: 217

Leu Phe Pro Leu Pro Leu Phe Leu
 1               5

<210> SEQ ID NO 218
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 218
ctattcccct ggacatacca actt                                           24

<210> SEQ ID NO 219
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 219

Leu Phe Pro Trp Thr Tyr Gln Leu
 1               5

<210> SEQ ID NO 220
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 220
cttattatga actggcctac atat                                           24

<210> SEQ ID NO 221
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 221

Leu Thr Met Asn Trp Pro Thr Tyr
 1               5

<210> SEQ ID NO 222
<211> LENGTH: 24
<212> TYPE: DNA
<213> ORGANISM: Artificial Sequence
<220> FEATURE:
<221> NAME/KEY: misc_feature
<222> LOCATION: (10)
<223> OTHER INFORMATION: n = a single nucleotide
<220> FEATURE:
<223> OTHER INFORMATION: Description of Artificial Sequence:Random
      nucleotide sequences.

<400> SEQUENCE: 222

```
tatattttcn cgctgagctt atca                                              24
```

<210> SEQ ID NO 223
<211> LENGTH: 7
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 223

Tyr Ile Phe Leu Ser Phe Ser
 1               5

<210> SEQ ID NO 224
<211> LENGTH: 24
<212> TYPE: DNA
<213> ORGANISM: Artificial Sequence
<220> FEATURE:
<223> OTHER INFORMATION: Description of Artificial Sequence:Random
      nucleotide sequences.

<400> SEQUENCE: 224

```
ctaacacccc tcccctcatg gcta                                              24
```

<210> SEQ ID NO 225
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 225

Leu Thr Pro Leu Pro Ser Trp Leu
 1               5

<210> SEQ ID NO 226
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 226

Leu Ile Cys Tyr Pro Leu Pro Thr
 1               5

<210> SEQ ID NO 227
<211> LENGTH: 8
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 227

Ile Pro Leu Tyr Leu Thr Cys Pro
 1               5

<210> SEQ ID NO 228
<211> LENGTH: 10
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 228

Ala Leu Leu Thr Gly Leu Phe Val Gln Asp
 1               5                  10

<210> SEQ ID NO 229
<211> LENGTH: 9
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 229

Ala Leu Leu Thr Gly Leu Phe Val Gln
 1               5

<210> SEQ ID NO 230
<211> LENGTH: 9
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 230

Ala Leu Leu Thr Gly Leu Phe Val Asp
 1               5

<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 231

Ala Leu Leu Thr Gly Leu Phe Gln Asp
 1               5

<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 232

Ala Leu Leu Thr Gly Leu Val Gln Asp
 1               5

<210> SEQ ID NO 233
<211> LENGTH: 9
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 233

Ala Leu Leu Thr Gly Phe Val Gln Asp
 1               5

<210> SEQ ID NO 234
<211> LENGTH: 10

```
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 234

Ala Leu Leu Thr Gly Leu Phe Val Gln Ala
 1               5                  10

<210> SEQ ID NO 235
<211> LENGTH: 10
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 235

Ala Leu Leu Thr Gly Leu Phe Val Ala Asp
 1               5                  10

<210> SEQ ID NO 236
<211> LENGTH: 10
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 236

Ala Leu Leu Thr Gly Leu Phe Ala Gln Asp
 1               5                  10

<210> SEQ ID NO 237
<211> LENGTH: 10
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 237

Ala Leu Leu Thr Gly Leu Ala Val Gln Asp
 1               5                  10

<210> SEQ ID NO 238
<211> LENGTH: 13
<212> TYPE: PRT
<213> ORGANISM: Artificial Sequence
<220> FEATURE:
<223> OTHER INFORMATION: Description of Artificial Sequence:Random
      peptide sequences.

<400> SEQUENCE: 238

Leu Phe Val Gln Asp Tyr Leu Leu Pro Thr Cys Ile Pro
 1               5                  10
```